(12) United States Patent
Truitt et al.

(10) Patent No.: US 10,039,914 B2
(45) Date of Patent: Aug. 7, 2018

(54) CONNECTOR FOR TRANSFERRING FLUID

(71) Applicant: CareFusion 303, Inc., San Diego, CA (US)

(72) Inventors: Tim L. Truitt, Orange, CA (US); Alex Truman Mazza, Grand Terrace, CA (US); Cliff Colwell, Corona, CA (US)

(73) Assignee: CAREFUSION 303, INC., San Diego, CA (US)

( * ) Notice: Subject to any disclaimer, the term of this patent is extended or adjusted under 35 U.S.C. 154(b) by 74 days.

(21) Appl. No.: 15/178,430

(22) Filed: Jun. 9, 2016

(65) Prior Publication Data
US 2016/0287858 A1 Oct. 6, 2016

Related U.S. Application Data

(63) Continuation of application No. 14/172,766, filed on Feb. 4, 2014, now Pat. No. 9,393,398, which is a
(Continued)

(51) Int. Cl.
| | |
|---|---|
| *A61M 39/10* | (2006.01) |
| *A61M 39/02* | (2006.01) |
| *A61M 39/22* | (2006.01) |
| *F16K 15/14* | (2006.01) |
| *A61M 39/24* | (2006.01) |
| *A61M 39/26* | (2006.01) |
| *F16K 15/02* | (2006.01) |
| *F16K 15/03* | (2006.01) |

(52) U.S. Cl.
CPC .......... *A61M 39/105* (2013.01); *A61M 39/02* (2013.01); *A61M 39/0208* (2013.01); *A61M 39/225* (2013.01); *F16K 15/141* (2013.01); *F16K 15/142* (2013.01); *A61M 39/24* (2013.01); *A61M 39/26* (2013.01); *F16K 15/023* (2013.01); *F16K 15/03* (2013.01); *Y10T 137/0318* (2015.04); *Y10T 137/7838* (2015.04); *Y10T 137/7842* (2015.04); *Y10T 137/7845* (2015.04); *Y10T 137/7879* (2015.04); *Y10T 137/86493* (2015.04); *Y10T 137/87571* (2015.04); *Y10T 137/87652* (2015.04); *Y10T 137/87684* (2015.04); *Y10T 137/9029* (2015.04)

(58) Field of Classification Search
CPC .. F16K 15/141; F16K 15/142; A61M 39/105; A61M 39/225; A61M 39/0208
USPC ...................................... 251/149.6
See application file for complete search history.

(56) References Cited

U.S. PATENT DOCUMENTS

| | | |
|---|---|---|
| 4,246,932 A | 1/1981 | Raines |
| 4,468,224 A | 8/1984 | Enzmann et al. |
| | (Continued) | |

*Primary Examiner* — Kevin Lee
(74) *Attorney, Agent, or Firm* — McDermott Will & Emery LLP

(57) ABSTRACT

A connector for transferring fluid, the connector may have a first port, a second port, and a third port which may be fluidly coupled together at an internal chamber with a first valve element therein controlling fluid flow through the second port. The connector can have ribs extending along the internal chamber to provide a fluid path around the valve element and between the first port and the internal chamber. The valve element can separate the internal chamber into an air chamber and a liquid chamber, and the third port can be continuously coupled to the liquid chamber regardless of a position of the valve element.

20 Claims, 16 Drawing Sheets

Related U.S. Application Data continuation of application No. 13/039,956, filed on Mar. 3, 2011, now Pat. No. 8,640,725, which is a continuation of application No. 12/538,686, filed on Aug. 10, 2009, now Pat. No. 7,909,056, which is a continuation of application No. 10/914,797, filed on Aug. 9, 2004, now Pat. No. 7,600,530.

(56) References Cited

U.S. PATENT DOCUMENTS

| | | | |
|---|---|---|---|
| 4,666,429 A | 5/1987 | Stone | |
| 4,919,167 A | 4/1990 | Manska | |
| 5,230,706 A | 7/1993 | Duquette | |
| 5,242,432 A | 9/1993 | DeFrank | |
| 5,300,034 A | 4/1994 | Behnke et al. | |
| 5,360,413 A | 11/1994 | Leason et al. | |
| 5,520,664 A | 5/1996 | Bricault, Jr. et al. | |
| 5,676,346 A | 10/1997 | Leinsing | |
| 5,730,418 A | 3/1998 | Feith et al. | |
| 5,749,861 A | 5/1998 | Guala et al. | |
| 5,782,816 A | 7/1998 | Werschmidt et al. | |
| 6,364,861 B1 | 4/2002 | Feith et al. | |
| 6,651,956 B2 | 11/2003 | Miller | |
| 7,160,272 B1 | 1/2007 | Eyal et al. | |
| 7,184,825 B2 | 2/2007 | Leinsing et al. | |
| 8,186,384 B2 | 5/2012 | Fujii et al. | |
| 8,257,320 B2 | 9/2012 | Feith et al. | |
| 8,640,725 B2 | 2/2014 | Truitt et al. | |
| 2005/0171489 A1 | 8/2005 | Weaver et al. | |
| 2006/0089603 A1 | 4/2006 | Truitt et al. | |
| 2006/0108554 A1* | 5/2006 | Enerson et al. | F16K 15/141 251/149.7 |

\* cited by examiner

CONNECTOR FOR TRANSFERRING FLUID

CROSS-REFERENCE TO RELATED APPLICATIONS

This application is a continuation of U.S. application Ser. No. 14/172,766, filed Feb. 4, 2014, U.S. Pat. No. 9,393,398, entitled "CONNECTOR FOR TRANSFERRING FLUID AND METHOD OF USE," which is a continuation of U.S. application Ser. No. 13/039,956, filed Mar. 3, 2011, U.S. Pat. No. 8,640,725, entitled, "CONNECTOR FOR TRANSFERRING FLUID AND METHOD OF USE," which is a continuation of U.S. application Ser. No. 12/538,686, filed Aug. 10, 2009, U.S. Pat. No. 7,909,056, entitled, "CONNECTOR FOR TRANSFERRING FLUID AND METHOD OF USE," which is a continuation of U.S. application Ser. No. 10/914,797, filed Aug. 9, 2004, U.S. Pat. No. 7,600,530, entitled, "CONNECTOR WITH CHECK VALVE AND METHOD OF USE," the disclosure of which is incorporated herein by reference in its entirety.

TECHNICAL FIELD

The present description is directed to a connector and method for transferring fluids and, in particular, a connector which incorporates a needleless access device to transfer fluid.

BACKGROUND OF THE INVENTION

Needleless access devices are used to inject medications or other fluids into a patient or withdraw fluids from a patient. These devices have valves therein that are actuated, for example, by insertion of a male luer of a syringe into the device. The needleless access devices form part of an intravenous tubing set, which comprises a length of tubing, a primary needle or catheter, and/or other connectors. One end of a length of tubing is attached to the primary needle or catheter, which is stuck into a vein of the patient. The other end of the tubing can be connected to the needleless access device. Alternatively, the needleless access device can be connected directly to the primary needle or catheter. Such a configuration allows all injections/withdrawal of fluid to be made through the needleless access device. Thus, needless access devices eliminate the need for repeated needle sticks into the patient, thereby avoiding unnecessary trauma to the patient. In addition, needleless access devices prevent needle stick injuries and the possibility of transmitting blood borne pathogens to healthcare professionals.

Needless access devices can also take the form of a Y-connector having first and second inlet ports, an outlet port, and a valve located in the first inlet port. The outlet port of the Y-connector is connected by an intravenous tube to a primary needle or catheter, which is inserted into a patient. And, the second inlet port is connected via an intravenous tube to an intravenous bag. Such a configuration forms the main intravenous line. The first inlet port, which contains the valve, can be used to inject fluids and/or medication into the main intravenous line from a syringe or piggyback intravenous bag. Similar to other needleless access devices, the valve in the first inlet port of the Y-connector is actuated, for example, by insertion of a male luer of a syringe into the Y-connector.

Backflow check valves have also been used in medical connectors. Backflow check valves allow for flow of fluid in one direction while preventing flow of fluid in the other direction (i.e., backflow). For example, when a connector is placed along the path of fluid flow from an intravenous bag to a patient, the check valve acts as a one way valve, allowing fluid to flow to the patient while, at the same time, preventing fluid and/or blood from flowing away from the patient. Moreover, check valves have been used in Y-connectors, which have a first and second inlet port, and an outlet port. The check valve is located in the first inlet port and is positioned between, for example, an intravenous bag and the patient (i.e., the main intravenous line). The check valve allows fluid to flow from the intravenous bag to the patient. Additional fluids can be injected into the main intravenous line through the second inlet port. When fluid is injected into the second inlet port, the check valve blocks fluid from flowing around the check valve in a direction away from the patient and towards the intravenous bag.

BRIEF SUMMARY OF THE INVENTION

The present invention relates to a connector for transferring fluids. In particular, the connector of the present invention incorporates a needleless access device and a backflow check valve. The connector may comprise a housing having a first port, a second port, and a third port. A first valve element may be positioned in the first port and a second valve element may be positioned in the second port. A first fluid may flow between the first port and the third port. A second fluid may be introduced into the connector via the second port and can combine with the first fluid. Alternatively, the first fluid may be removed from the connector through the second port.

The present invention also relates to a method of transferring fluid. The first valve element may be in a first position in the first port as a first fluid flows between the first port and the third port. A fluid transfer device may be inserted into the second port to actuate the second valve element. Upon insertion of the fluid transfer device into the second port, the second valve element can move from a first position where the second port is closed (i.e., fluid cannot be injected into/withdrawn from the second port) to a second position where the second port is open (i.e., fluid can be injected into/withdrawn from the second port). And, when the fluid transfer device is removed from the second port, the second valve element may move from the opened position to the closed position. In the open position, a second fluid may be transferred between the fluid transfer device and the connector via the second port or the first fluid may be withdrawn from the connector. If a second fluid is transferred into the connector through the second port, the first valve element may move from the first position to a second position. In the second position, fluid may be prevented from flowing past the first valve element. Alternatively, if a first fluid is withdrawn from the connector through the second port, the first valve element may remain in the first position.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which.

DETAILED DESCRIPTION OF THE INVENTION

Figure 1:
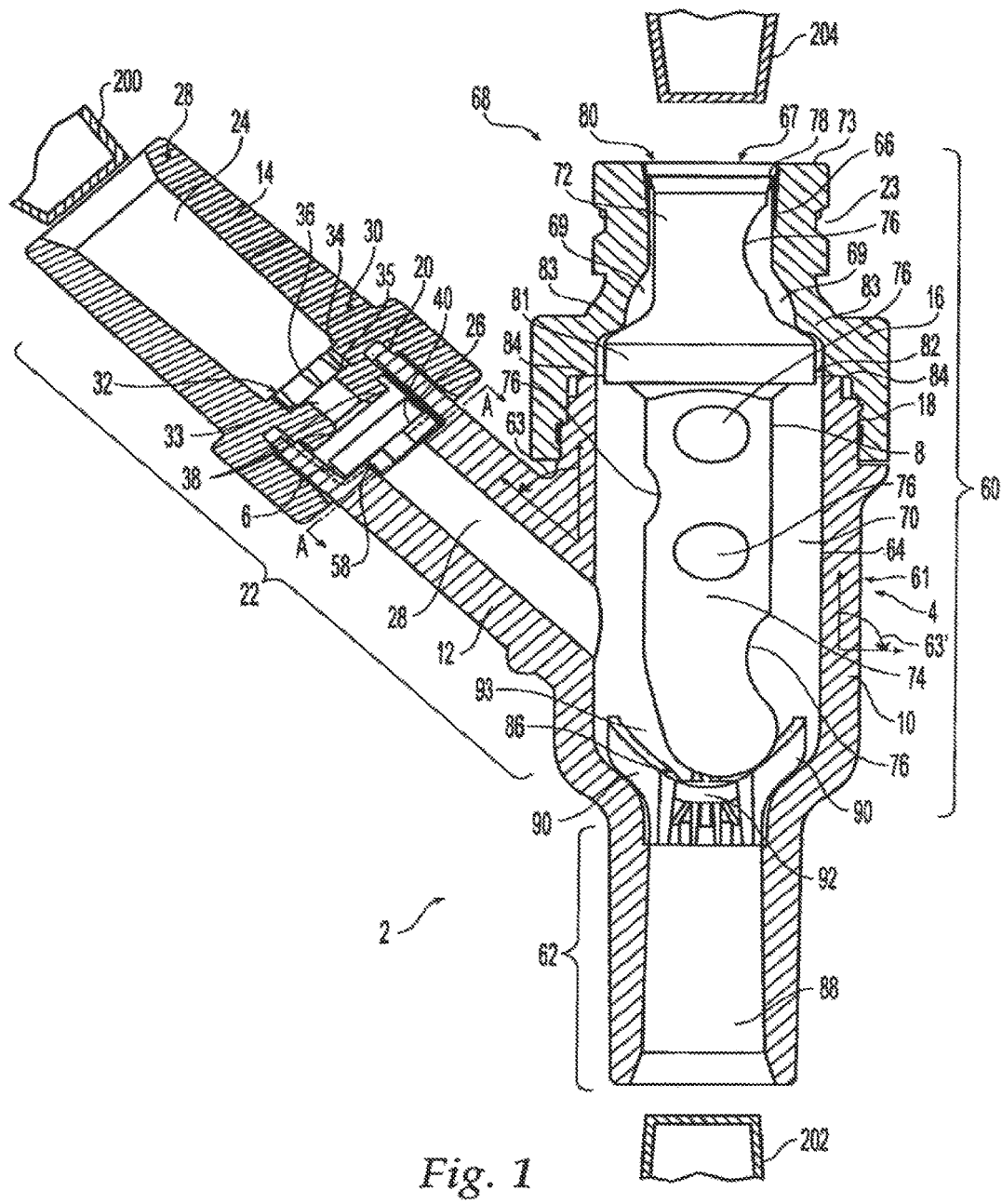
FIG. 1 is a partial cross-sectional view of an exemplary embodiment of the connector of the present invention.

FIG. 1 shows an exemplary embodiment of a connector 2 for transferring fluid. The term "fluid" may include, for example, blood, medication, saline, water, oxygen or other gas, air (i.e., a mixture of gases).

Figures 2, 2A:
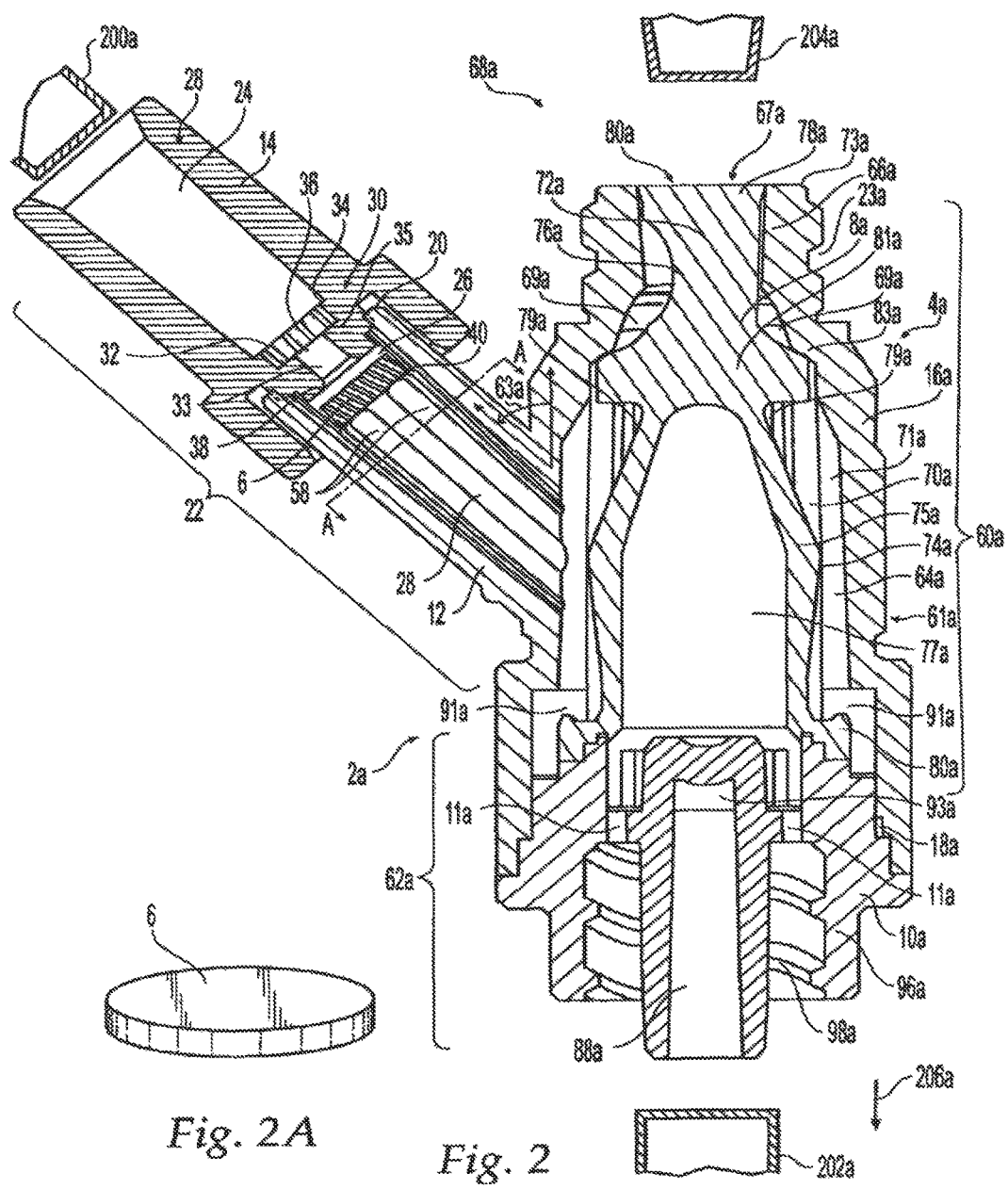
FIG. 2 is a cross-sectional view of an alternative exemplary embodiment of the connector of the present invention.
FIG. 2A is a perspective view of an exemplary embodiment of a valve element of FIGS. 1 and 2.

The connector 2 of the present invention may comprise a housing 4, a first valve element 6, and a second valve element 8. It should, however, be understood that those of ordinary skill in the art will recognize many modifications and substitutions which may be made to various elements of the present invention. The housing 4 may comprise a base portion 10, an offshoot 12, a first cap 14 and a second cap 16. In another embodiment of the present invention, as shown in FIG. 2, the connector 2a may comprise a housing 4a, a first valve element 6, and a second valve element 8a. The housing 4a may comprise a base portion 10a, an offshoot 12, a first cap 14 and a second cap 16a. The base portion 10, offshoot 12, first cap 14 and second cap 16 of FIG. 1 may be made of, for example, metal, plastic (e.g., polycarbonate, acrylonitrile butadiene styrene (ABS)), a composite material (i.e., two or more materials) (e.g., copolyester), or rubber. The same materials may be used for the base portion 10a, offshoot 12, first cap 14 and second cap 16a of FIG. 2. Moreover, the base portion 10, base portion 10a, offshoot 12, first cap 14, second cap 16 and/or second cap 16a may be made of the same or different materials and may be transparent or opaque. Various factors may be considered when determining the material to be used for the base portion 10, base portion 10a, offshoot 12, first cap 14, second cap 16 and/or second cap 16a, including compatibility with fluids flowing through the connector 2, 2a (i.e., material does not chemically and/or physically react with fluids flowing through the connector 2, 2a) (e.g., lipid resistance), the ability to withstand sterilization/cleaning (i.e., cleaning products used in sterilization), weight, durability, mechanical strength, resistance to bacterial formation, ease and cost of manufacturing, and ability to be attached to other materials. And, while the base portion 10, base portion 10a, offshoot 12, first cap 14, second cap 16 and/or second cap 16a are shown as cylindrical in FIGS. 1 and 2, the base portion 10, base portion 10a, offshoot 12, first cap 14, second cap 16 and/or second cap 16a may be any shape (e.g., polygonal). Various factor may be considered when determining the shape of the base portion 10, base portion 10a, offshoot 12, first cap 14, second cap 16 and/or second cap 16a, including the compatibility with standard fluid transfer devices (e.g., an intravenous tube, syringe, catheter or other connector), the desired path of fluid flow, ability of the connector 2, 2a to be flushed, and clearance around internal components (e.g., the valve elements 6 and 8, 8a).

Additionally, the base portion 10, base portion 10a, offshoot 12, first cap 14, second cap 16 and/or second cap 16a may be made, for example, by injection molding, extrusion, casting, compression molding or transfer molding and can be constructed as a single piece or may be separate pieces attached together by, for example, bonding medium (e.g., adhesive), threads, ultrasonic welding, ultraviolet curing, tape, corresponding clip and clip engaging portion(s) (e.g., a snap connection), spin welding or otherwise melting together. For example, in an embodiment of FIG. 1, the base portion 10 and offshoot 12 may have external threads (not shown) on external portions 18 and 20, respectively, to engage internal threads (not shown) of the second cap 16 and the first cap 14, respectively. Similarly, in one embodiment of FIG. 2, the base portion 10a and offshoot 12 may have external threads (not shown) on external portions 18a and 20, respectively, to engage internal threads (not shown) of the second cap 16a and the first cap 14, respectively. In another embodiment of FIGS. 1 and 2, the base portion 10, 10a and offshoot 12 may be separate pieces attached together either permanently or removeably by any of the attachment means described above. Moreover, a washer (not shown) (e.g., an O-ring) may be positioned between the base portion 10 and the second cap 16, the base portion 10a and the second cap 16a, the offshoot 12 and the first cap 14, and/or the base portion 10, 10a and the offshoot 12 to prevent fluid from leaking out of connector 2, 2a.

Alternatively, the connector 2, 2a may be molded or otherwise formed, for example, in two halves, which may be joined together by any of the means described above. In one embodiment, the base portion 10, base portion 10a, offshoot 12, first cap 14, second cap 16 and/or second cap 16a may be joined using one or more hinges (not shown). In general, a separate piece construction may allow for replacement of parts within the connector 2, 2a (e.g., the first valve element 6 and/or the second valve elements 8, 8a) and/or cleaning the inside of connector 2, 2a.

As shown in FIGS. 1 and 2, the connector 2, 2a may comprise a first port 22. All discussion herein regarding the first port 22 applies to the embodiments shown in both FIGS. 1 and 2. And, even though the construction of the first port 22 of FIGS. 3A, 3B, 4A, 4B, 5A, 5B, 6A, 6B, 8 and 9 are shown in the context of the connector 2 of FIG. 1, it should be understood that these constructions also may be incorporated in the construction of the connector 2a of FIG. 2.

The first port 22 may comprise the offshoot 12 and the first cap 14. The first port 22 may have a first channel portion 24, a main channel portion 26 containing the first valve element 6, and a connecting channel 28. The first valve element 6, however, may be located anywhere in the first port 22. The first port 22 may be constructed to receive a fluid transfer device (e.g., an intravenous tube, syringe, catheter or other connector). The fluid transfer device may be connected to the inside or outside of the first port 22. For example, the first cap 14 of the first port 22 may have external or internal threads to engage corresponding threads of a fluid transfer device. In another embodiment, the first port 22 may be connected to a fluid transfer device using a clip (not shown) on the connector 2, 2a that engages a clip receiving portion (not shown) on the fluid transfer device (i.e., a snap connection) or vice versa. In yet another embodiment, a fluid transfer device may be connected to the cap 14 by, for example, a bonding medium (e.g., adhesive), ultrasonic welding, ultraviolet curing, tape, spin welding or otherwise melting together. However, the present invention envisions all temporary and permanent means of attaching a fluid transfer device to the first port 22.

The first channel portion 24 may be any shape (e.g., cylindrical or polygonal), may taper from a proximal portion 28 to a distal portion 30 and/or may have sections with varying diameters. Various factors may be considered when determining the shape of the first channel portion 24, including the compatibility with a standard fluid transfer device (e.g., an intravenous tube, syringe, catheter or other connector), the desired path of fluid flow, and ability of the connector 2, 2a to be flushed. For example, as shown in FIGS. 1 and 2 the first channel portion 24 may have reduced diameter portions 32 and/or 33. One reason for providing reduced diameter portions 32 and/or 33 may be to form ledges 34 and/or 35, respectively, against which a fluid transfer device may abut. Such a construction may limit the distance that a fluid transfer device may be inserted into the first port 22. And, as will become apparent from the discussion below, another reason for reduced diameter portions 32 and/or 33 may be to provide a means by which valve element 22 may control fluid flow.

The first channel portion 24 may also have one or more bonding medium reservoirs 36 which may take the form of one or more recesses or grooves in the first channel portion 24 and, in particular, in the reduced diameter portion 32. The bonding medium reservoirs 36 may also be located on the outside of the first port 22 in those embodiments where a fluid transfer device is connected to the outside of the first port 22. The bonding medium reservoirs 36 may receive excess bonding medium (e.g., adhesive) when a fluid transfer device is positioned in the first channel portion 24 or on the outside of the first port 22 using a bonding medium. It should be understood that a bonding medium reservoir may receive any liquid material which may harden, including any solid material (e.g., solid plastic) that has been melted (e.g., as may result if a fluid transfer device is ultrasonically welded to the first port 22). Another function of the bonding medium reservoirs 36 may also be to prevent bonding medium and/or melted material from spreading into other portions of the first port 22 such as the main channel portion 26 and/or the connecting channel 28. Such a construction may be advantageous because bonding medium and/or melted material may affect the movement of the first valve element 6 and/or the overall flow of fluid through the first port 22.

The first valve element 6 may be positioned in the first port 22 and, in particular, in the main channel portion 26. The first valve element 6 may be made of plastic, a foam material, a composite material (i.e., two or more materials), a combination material (i.e., one material contained within another material) (e.g., a gel such as a hydrogel contained within rubber) or rubber (e.g., silicon polyisoprene) and may be formed, for example, by injection molding, extruded, casting, compression molding or transfer molding. Various factors may be considered when determining the material to be used to make the first valve element 6, including compatibility with fluid flowing through the connector 2, 2a (i.e., material does not chemically and/or physically react with fluids flowing through the connector 2, 2a) (e.g., lipid resistance), the ability to withstand sterilization/cleaning (i.e., cleaning products used in sterilization in a hospital), weight, durability, mechanical strength, resistance to bacterial formation, ease and cost of manufacturing, ability to withstand staining (i.e., from blood or other chemical products used in a hospital), ability to float in fluids, and mechanical properties (e.g., resiliency; ability to be compressed, bent, folded, or otherwise contorted). And, while the first valve element 6 may be made of a material that is impermeable to fluid (i.e., does not allow fluid to pass into or through the first valve element 6 in any substantial way), the first valve element 6 may also be made of a material that is fluid permeable (i.e., allows fluid to pass into or through the first valve element 6). Moreover, the first valve element 6 may be transparent or opaque, flexible or rigid, and/or hard or soft.

As shown in FIG. 2A, the first valve element 6 may be a disc which may have a thickness between about 0.004 inches and about 0.250 inches, preferably between about 0.030 inches and about 0.20 inches, and, most preferably, between about 0.03 inches and about 0.05 inches. The first valve element 6 may have a diameter between about 0.02 inches and about 0.50 inches, preferably between about 0.05 inches and about 0.25 inches, and, most preferably, between about 0.12 inches and about 0.14 inches. Various factors may be relevant in determining the thickness and/or diameter of the first valve element 6, including rigidity, flexibility, permeability, compressibility and resiliency (i.e., ability to return to original orientation after compression).

The first valve element 6 may be any shape (e.g., cylindrical, spherical, square, rectangular, triangular, conical, or polygonal), may have flat surface(s), and/or may have concave/convex surface(s). In addition, the first valve element 6 may have protrusions (e.g., protrusions 56 in FIG. 6C), indentations or ridges on a portion thereof or over its entire surface. The advantage of such a construction is described below with reference to FIGS. 6A and 6B.

Figure 4A:
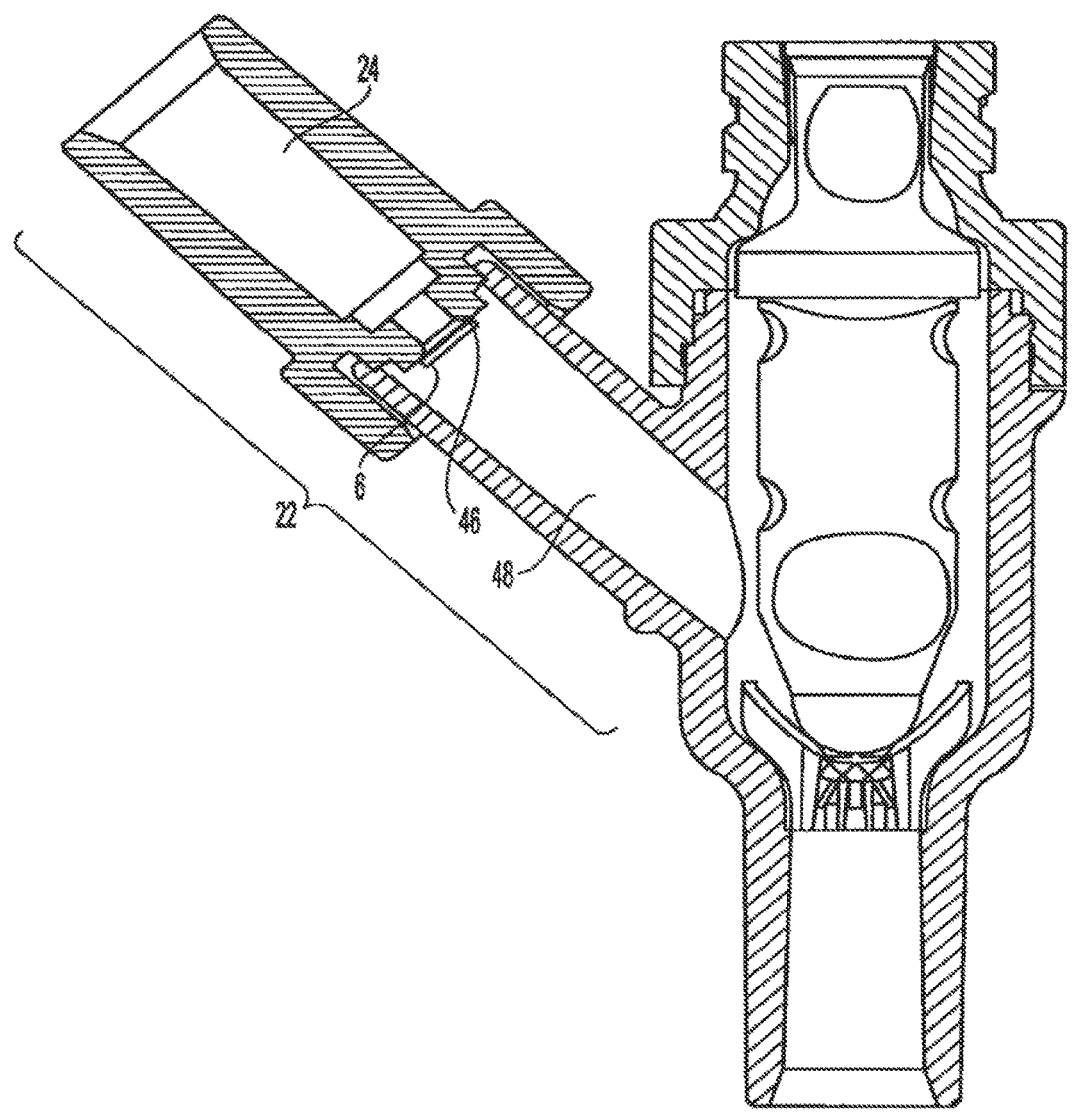
FIGS. 4A-4B are partial cross-sectional views of another alternative exemplary embodiment of the connector of FIG. 1 with another alternative first port construction.
Figure 4B:
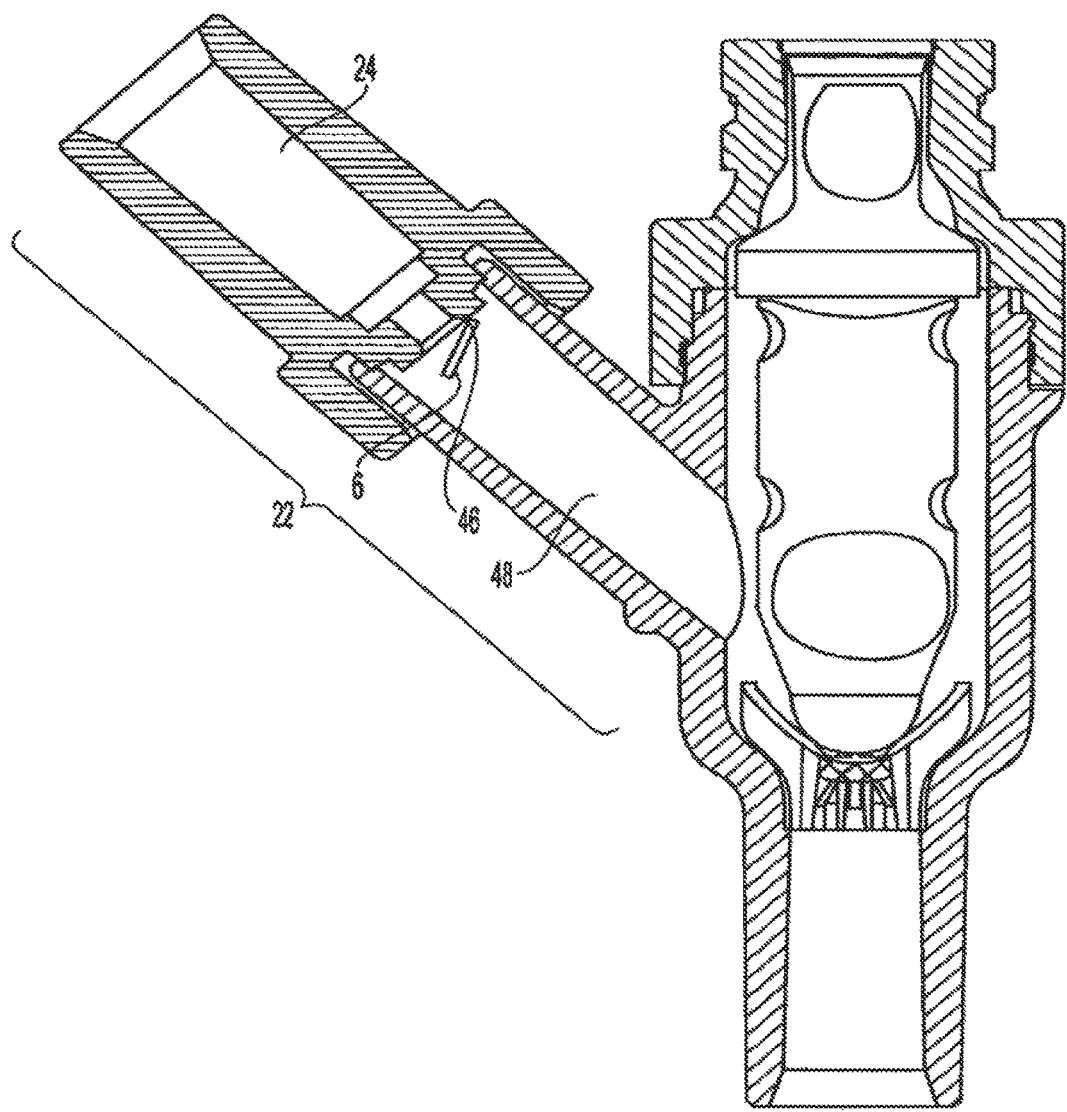

Moreover, as shown in FIGS. 1 and 2, the first valve element 6 may be freely moveable within the first port 22 (i.e., not fixedly attached to any other structure) or, as shown in FIGS. 4A and 4B, may be fixedly attached within the first port 22 such as, for example, by a hinge 46. The first valve element 6 may be positioned in the first port 22 in any way so long as fluid may flow past the valve element 6. It should be noted that the term "flow past" or any similar term using the word "past" or "pass" may mean fluid flows through or around any structure in the connector 2, 2a including any portion or the entirety of the first valve element 6 and/or the second valve element 8, 8a.

In FIGS. 1 and 2, the valve element 6 may move towards the reduced diameter portion 33 and may engage an upper stopping portion 38. In this position, fluid may be prevented from flowing past the valve element 6 (i.e., fluid may not be able to flow between the first channel portion 24 and the connecting channel 28). The first valve element 6 may also move away from the reduced diameter portion 33 and may engage a lower stopping portion 40. In this position, fluid may be able to flow past the valve element 6, for example, as will be described in detail below with reference to the fluid channels 58.

As shown in FIGS. 1 and 2, the main channel portion 26 may be larger than the first valve element 6 so that the first valve element 6 may move freely within the main channel portion 26. In an alternative embodiment, the main channel portion 26 may be substantially the same size and shape as the first valve element 6. In yet another embodiment, the main channel portion 26 may have fluid paths (not shown) through which fluid may flow past the first valve element 6. These fluid paths may extend around a portion or the entire periphery of the first valve element 6. In addition, the fluid paths may be one or more individual and separated fluid paths or may be one continuous flow path around the entire periphery of the first valve element 6.

Figure 3A:
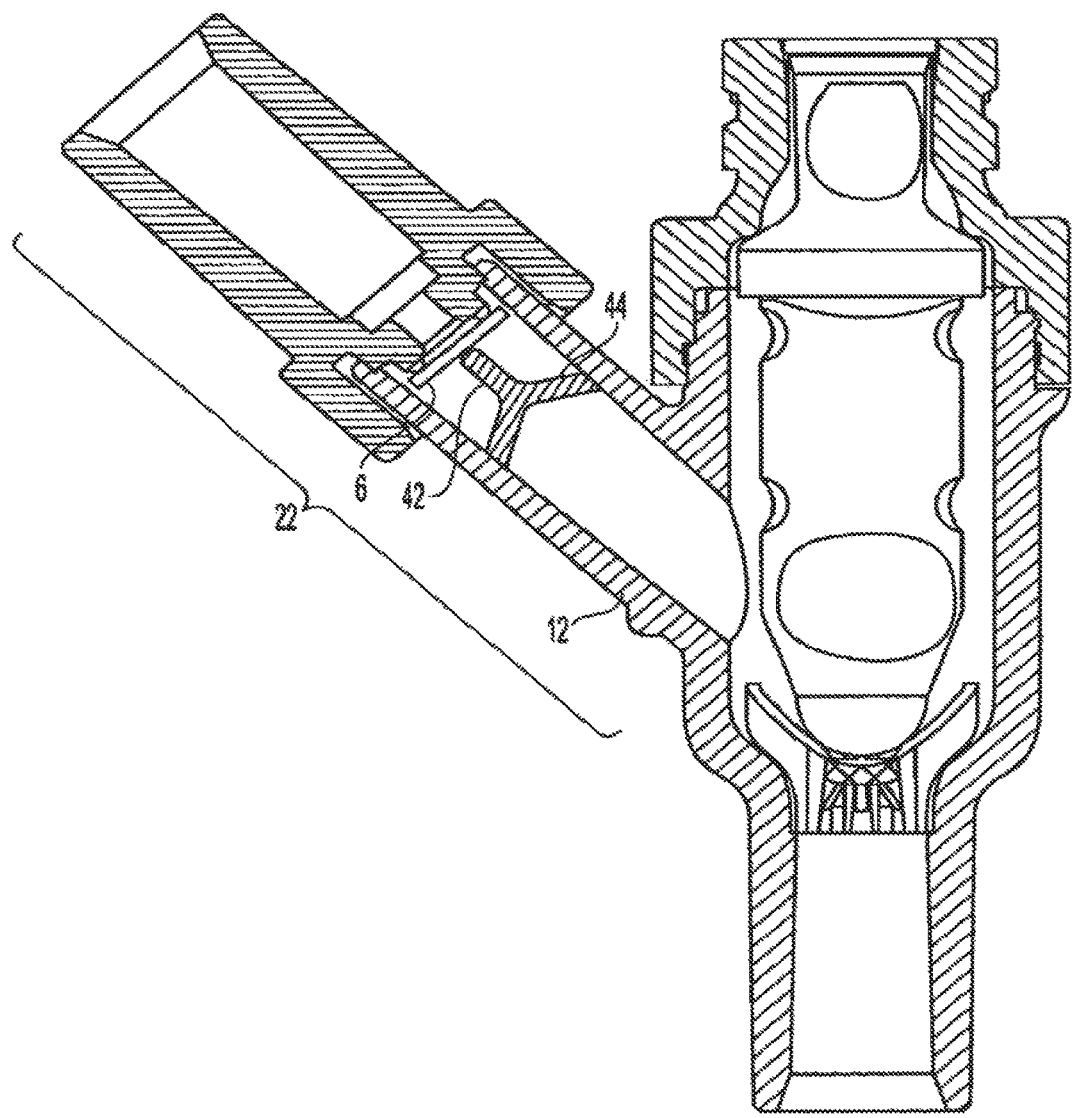
FIGS. 3A-3B are partial cross-sectional views of an alternative exemplary embodiment of the connector of FIG. 1 with an alternative first port construction.
Figure 3B:
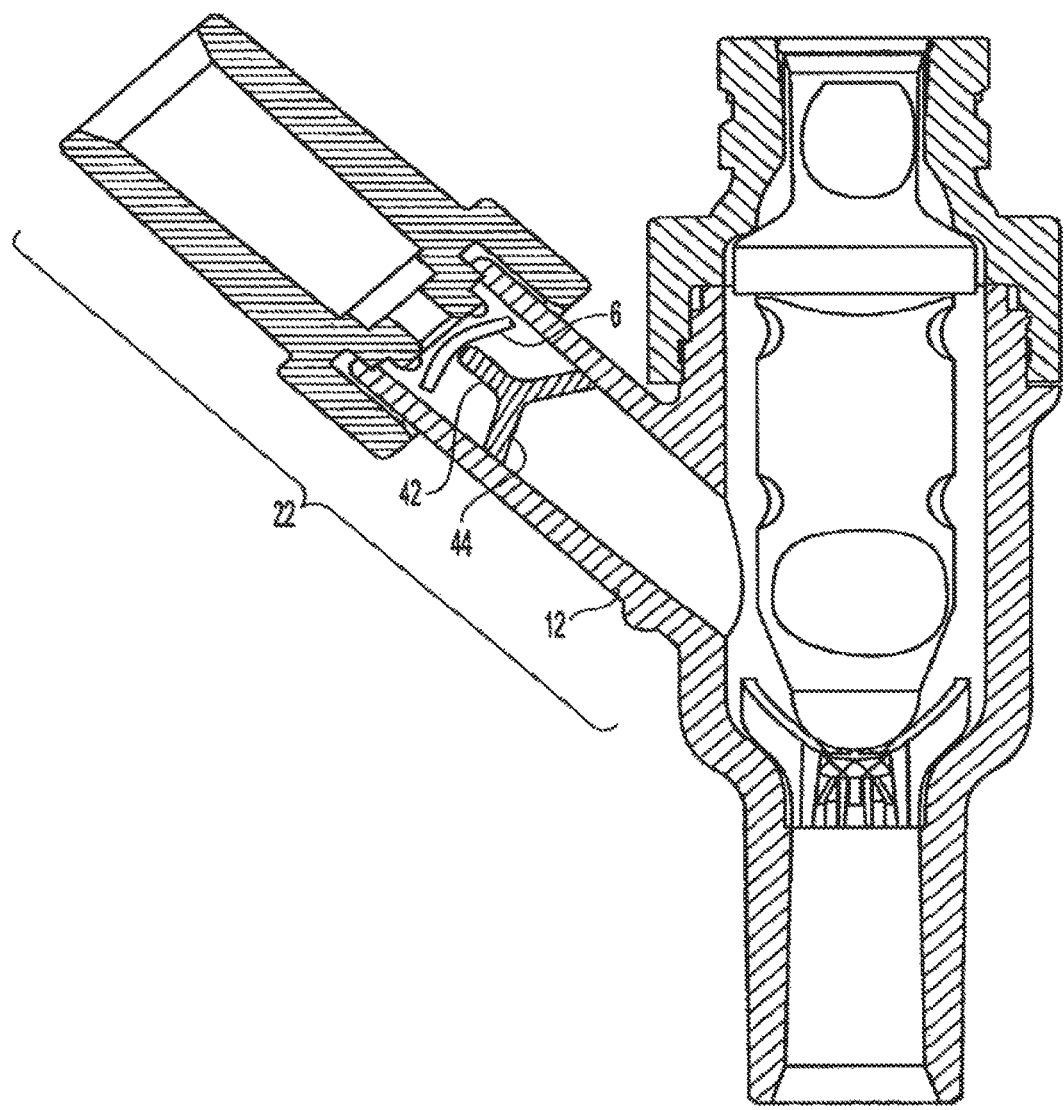

FIGS. 3A and 3B illustrate another embodiment of the construction of the first port 22. The first valve element 6 may be flexible and abutting one or more support elements 42 (e.g., prongs) positioned within the first port 22. For example, the support elements 42 may be attached to the offshoot 12 by a connecting portion 44. In one embodiment, the connecting portion 44 may be conical in shape and may have openings (not shown) which allow fluid to flow past connecting portion 44. The connecting portion 44, however, can be any structure, having any shape, that holds one or more support elements 42 within the first port 22. In use, the valve element 6 may move between an unflexed position (FIG. 3A), where fluid may be prevented from flowing past the first valve element 6, and a flexed position (FIG. 3B), where fluid may flow past the first valve element 6.

FIGS. 4A and 4B illustrate yet another embodiment of the construction of the first port 22. The first valve element 6 may be attached within the first port 22 using a hinge 46. In this embodiment, the first port 22 may comprise a first channel portion 24 and a channel 48. The channel 48 may be any size or shape so long as the first valve element 6 may move therein and allows fluid to flow past the first valve element 6. The first valve element 6 may move between a closed position (FIG. 4A), where fluid may be prevented from flowing past the first valve element 6 and an opening position (FIG. 4B), where fluid may flow past the first valve element 6.

Figures 5A, 5C:
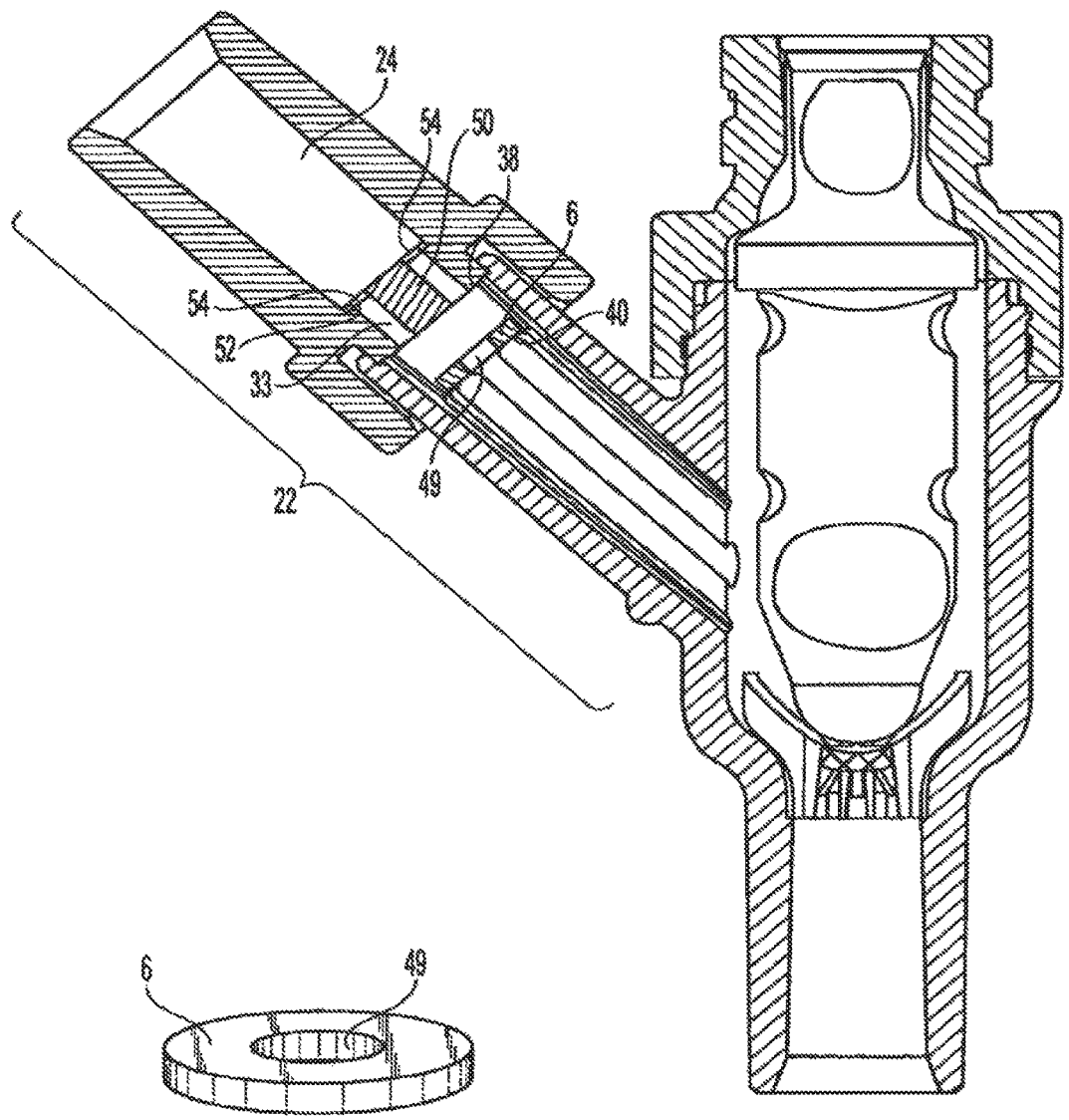
FIGS. 5A-5B are partial cross-sectional views of another alternative exemplary embodiment of the connector of FIG. 1 with another alternative first port construction.
FIG. 5C is a perspective view of an exemplary embodiment of a valve element of FIGS. 5A and 5B.
Figure 5B:
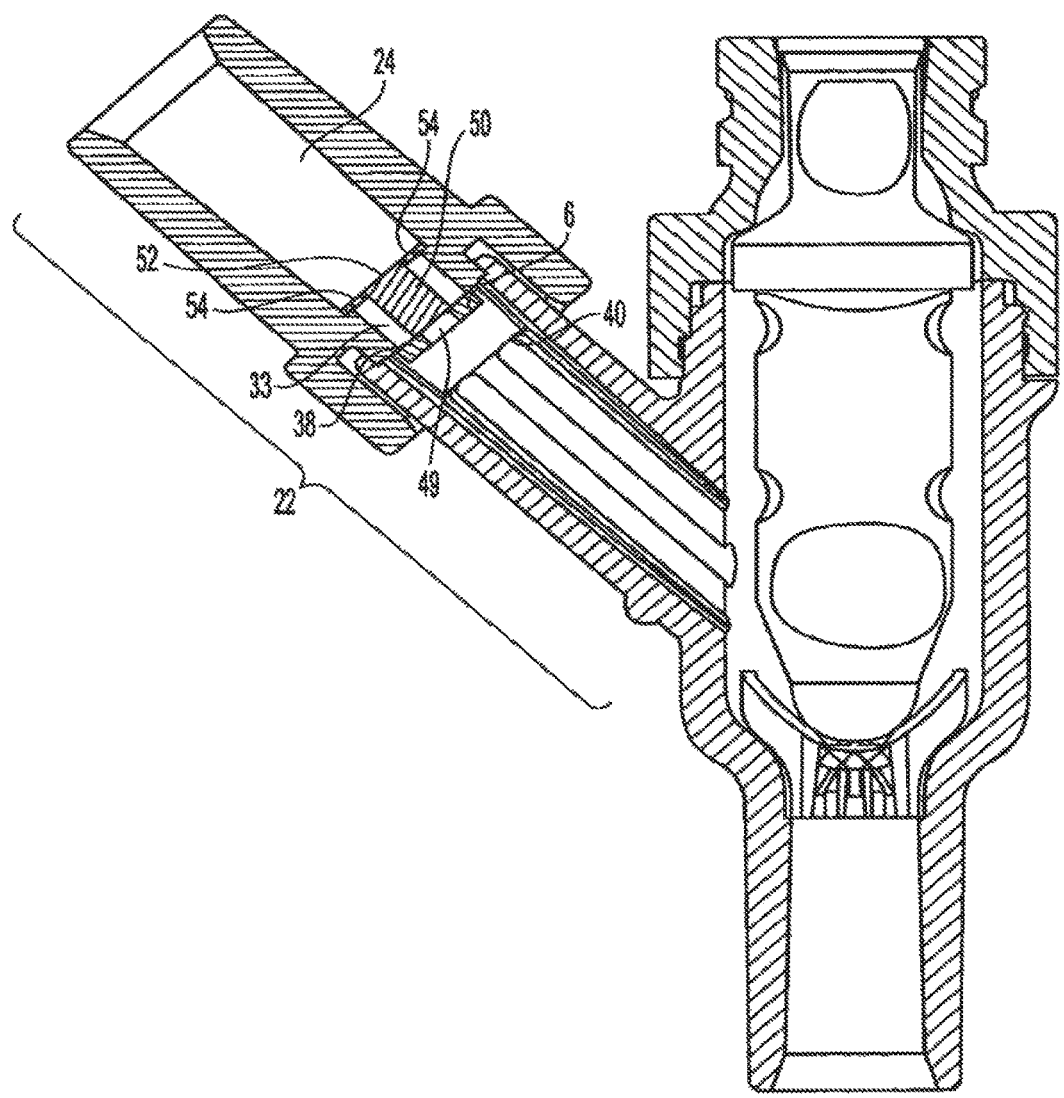

FIGS. 5A and 5B show another alternative embodiment of the construction of the first port 22. As illustrated in FIG. 5C, the first valve element 6 may have a hole or opening 49. The hole 49 may be any shape or size so long as fluid may flow through the first valve element 6. The first channel portion 24 may have a portion 50, which may be held within the first channel portion 24 by a connector 52. The connector 52 may be any shape (e.g., a disc shape) and may have one or more opening 54 to allow fluid to pass therethrough. It should be understood that the connector 52 may be any structure which can hold a portion 50 within the first port 22 and allow fluid to flow past a first valve element 6.

Moreover, the portion 50 may be any shape (e.g., circular, rectangular, square, triangular, conical, cylindrical, polygon) and may have a diameter greater than the diameter of the hole 49. It should be noted that the portion 50 may be any structure that engages with the first valve element 6 and can be used to control the flow of fluid past the valve element 6. In use, as shown in FIG. 5A, the first valve element 6 may move away from the reduced diameter portion 33 and may engage the lower stopping portion 40. In this position, fluid may flow past the first valve element 6. And, as shown in FIG. 5B, the first valve element 6 may move towards the reduced diameter portion 33 and may engage the upper stopping portion 38 and portion 50. In this position, fluid may be prevented from flowing past the first valve element 6.

Figures 6A, 6C:
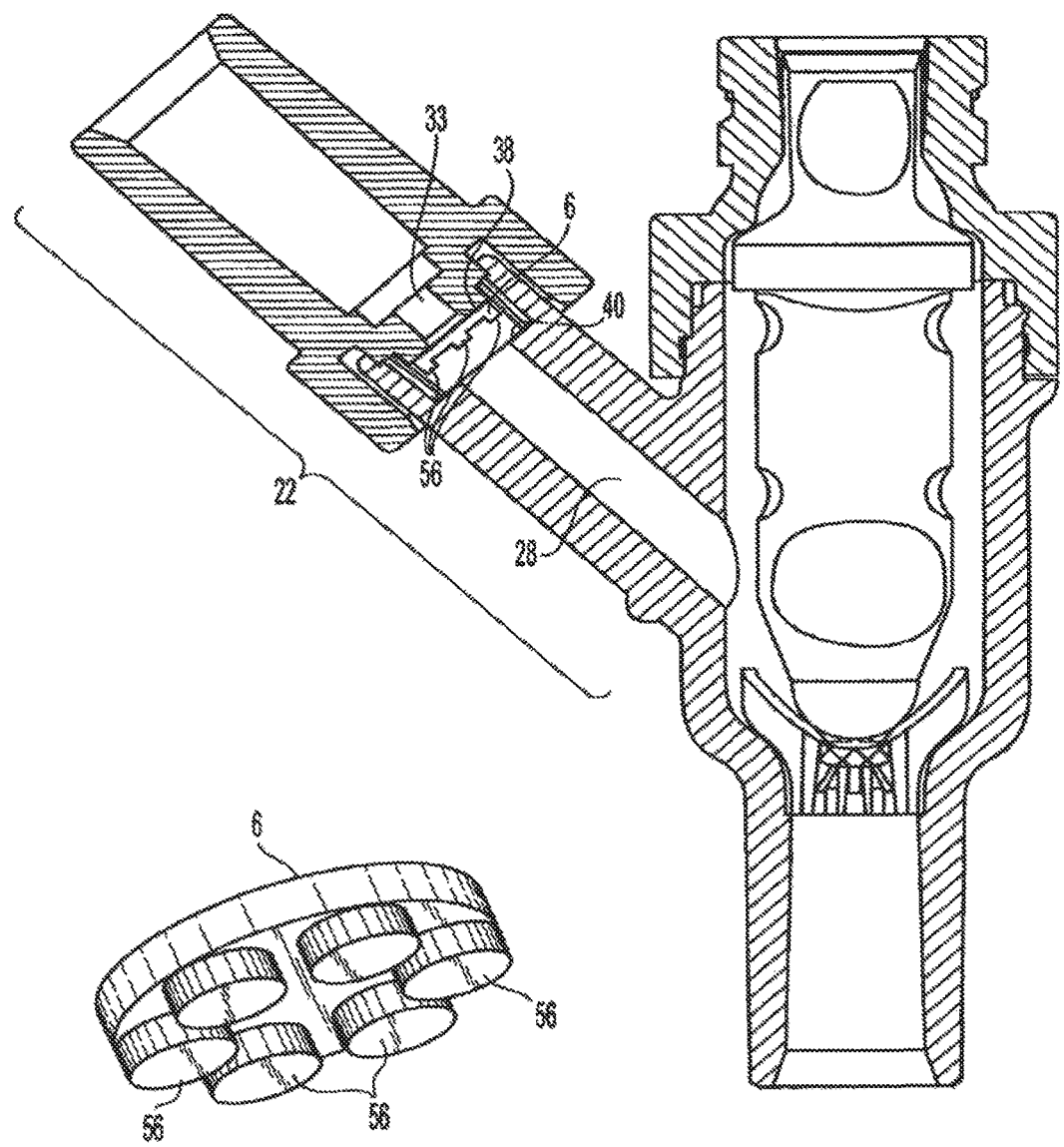
FIGS. 6A-6B are partial cross-sectional views of another alternative exemplary embodiment of the connector of FIG. 1 with another alternative first port construction.
FIG. 6C is a perspective view of an exemplary embodiment of a valve element of FIGS. 6A and 6B.
Figure 6B:
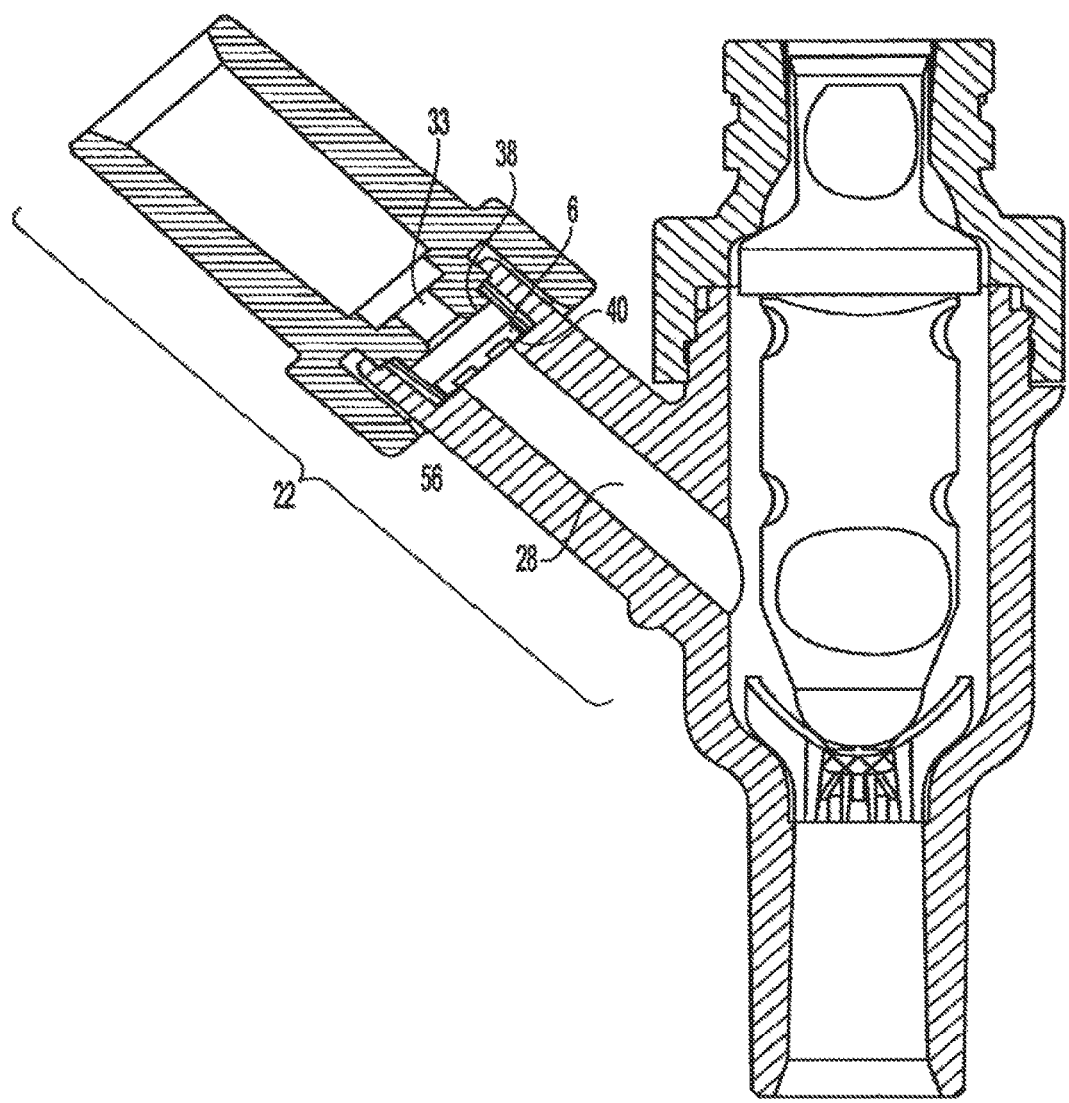

FIGS. 6A and 6B illustrate another exemplary embodiment of the construction of the first port 22 where the first valve element 6 may have one or more protrusions 56 (FIG. 6C). The protrusions 56 may be formed integrally with or may be attached to the first valve element 6. As shown in FIG. 6A, the first valve element 6 may move towards the reduced diameter portion 33 and abut the upper stopping portion 38. In this position, fluid may be prevented from flowing past the first valve element 6. As shown in FIG. 6B, the first valve element 6 may move away from the reduced diameter portion 33 and abut the lower stopping portion 40. In this position, fluid may flow past the first valve element 6. The stopping portion 40 may be a solid ledge and fluid may flow past the first valve element 6 by flowing in between protrusions 56 and into the connecting channel 28 (shown in FIGS. 6A and 6B). Alternatively, the stopping portion 40 may be made up of portions of a wall 59 between one or more fluid channels 58 (FIG. 7).

Figure 7:
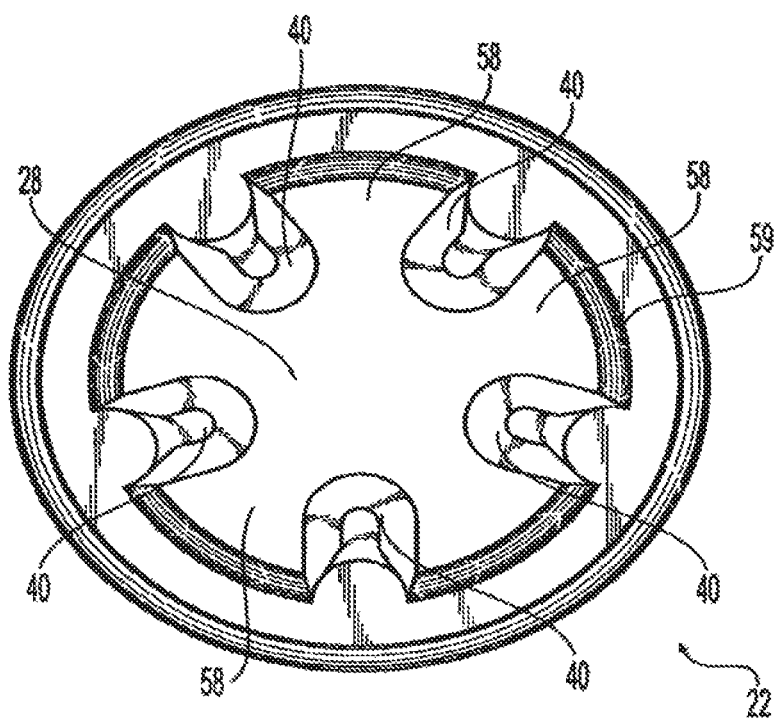
FIG. 7 is a partial cross sectional view of an exemplary embodiment of a first port of FIGS. 1 and 2 along A-A.
Figure 8:
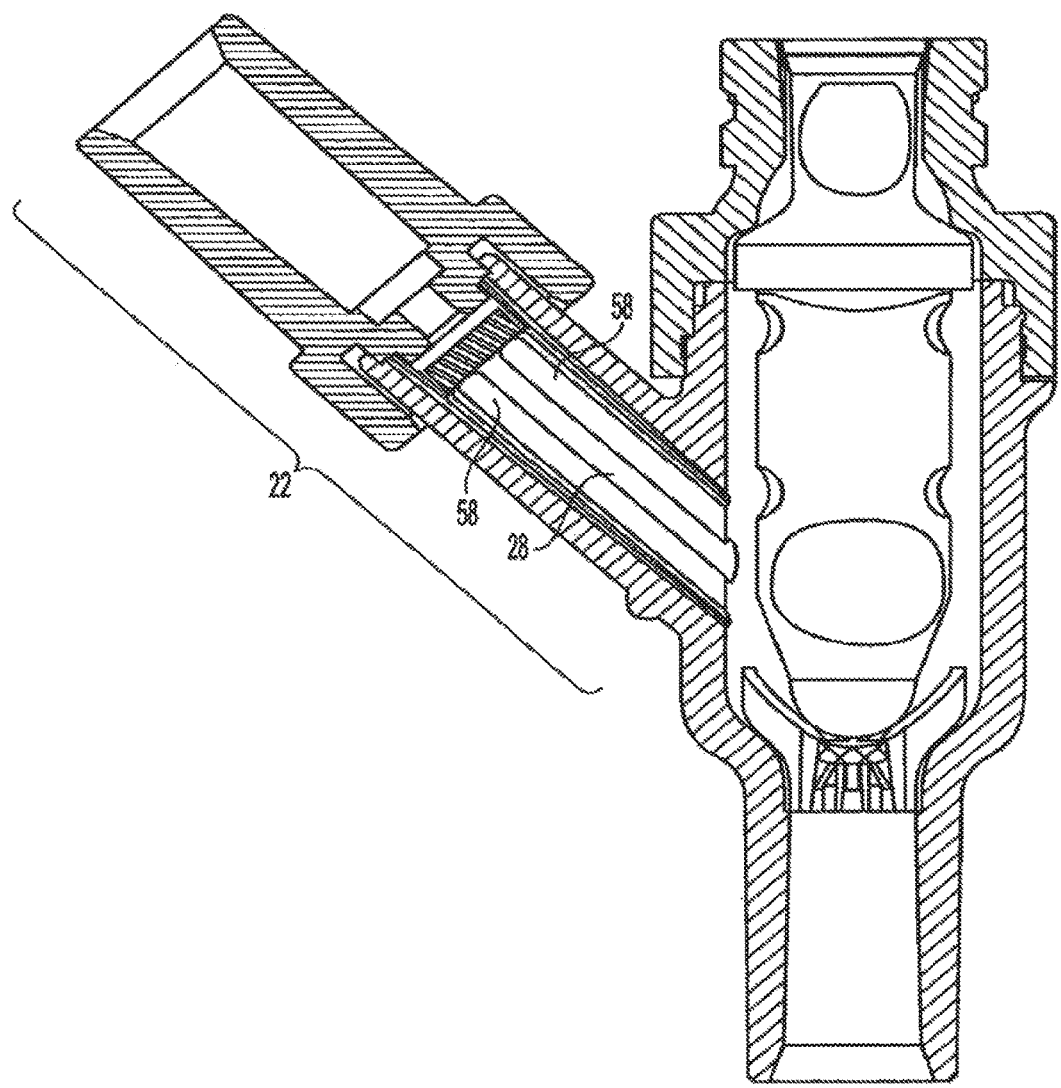
FIG. 8 is a partial cross-sectional view of an alternative exemplary embodiment of the connector of FIG. 1 with another alternative first port construction.

In any embodiment of the present invention, the first port 22 and, in particular, the connecting channel 28 may have one or more fluid channels 58 (as shown in FIG. 7 which is a view from A-A of FIGS. 1 and 2). The fluid flow channels 58 may allow fluid to flow past the first valve element 6 (e.g., around the first element 6). As shown in FIG. 7, the fluid channels 58 may be formed in the wall 59 of the first port 22. The fluid channels 58 may extend along a portion of the length of the first port 22 (shown in FIG. 1) or over a substantial length of the first port 22 (e.g., over substantially the entire length of the connecting channel 28 (shown in FIGS. 2 and 8)). As illustrated in FIG. 7, such a construction may form the lower stopping portion 40, which may abut with the first valve element 6. It should be noted, however, than any portion that abuts the first valve element 6 may be a lower stopping portion 40.

The shorter fluid channels 58 (such as those of FIG. 1) may be effective in controlling fluid flow past the first valve element 6 and into a connecting channel 28. This design may prevent the formation of air bubbles within the first port 22 (in particular, below the first valve element 6); air bubbles may present health risks to a patient (especially children and the elderly). In contrast, longer fluid channels 58 (such as those in FIG. 2) may not control the flow of fluid around the first valve element 6 as well as shorter fluid channels 58 and may result in air bubbles. Moreover, short fluid channels 58 may provide the additional advantages of reducing the priming and/or flush volumes, which may result in increased efficiency of fluid delivery to a patient. Other reasons for varying the length of the fluid channels 58 will also be appreciated by those skilled in the art. It should, however, be understood that the fluid channels 58 can extend any distance within the first port 22.

Further, the fluid channels 58 may be formed as part of the first port 22 or as part of a separate piece (not shown), which may be inserted into the first port 22. As part of the first port 22, the fluid channels 58 may be made of the same material as the first port 22. The separate piece may be made, for example, of metal, plastic (e.g., polycarbonate, acrylonitrile butadiene styrene (ABS)), a composite material (i.e., two or more materials) (e.g., copolyester) or rubber. The separate piece may be made of the same material as or a different material from the first port 22. Various factors may be considered when determining the material used for the separate piece, including compatibility with fluids flowing through the connector 2, 2*a* (i.e., the material does not react with fluids flowing through the connector 2, 2*a*) (e.g., lipid resistance), the ability to withstand sterilization/cleaning (i.e., cleaning products used in sterilization), weight, durability, mechanical strength, resistance to bacterial formation, ease and cost of manufacturing, and ability to be attached to other materials. The separate piece may be attached to the inner wall of first port 22, for example, by a bonding medium (e.g., adhesive), threads, ultrasonic welding, ultraviolet curing, corresponding clip and clip engaging portion (s) (e.g., a snap connection), spin welding or otherwise melting together. In an embodiment where an operator can gain access to the inside of the connector 2, the separate piece may be replaceable.

Figure 9:
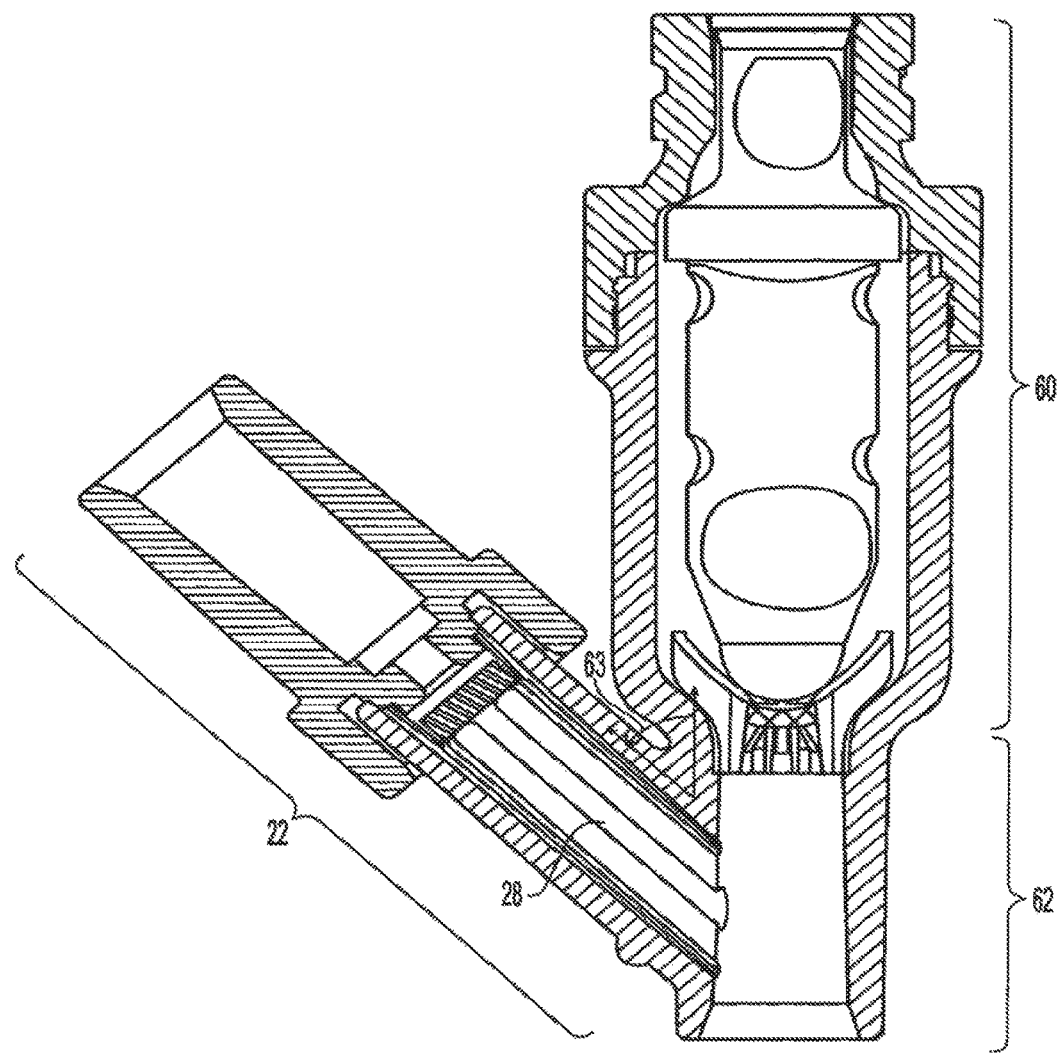
FIG. 9 is a partial cross-sectional view of an alternative exemplary embodiment of the connector of FIG. 8 with the first port located in an alternative position.

Turning now to the interconnection between ports, the first port 22 may be connected to a second port 60, 60*a* as shown in FIGS. 1 and 2, respectively. The second port 60, 60*a* may be integral with the first port 22 or may be attachable to the first port 22. Alternatively, as shown in the embodiment of FIG. 9, the first port 22 may be connected to the third port 62. Moreover, in one embodiment of FIG. 2, while not shown, the first port 22 may be connected to the third port 62*a*.

In an embodiment where the first port 22, second port 60, 60*a* and/or third port 62, 62*a* are all separate pieces, one port may be permanently or removeably connected to another port, for example, by a bonding medium (e.g., adhesive), threads, ultrasonic welding, ultraviolet curing, tape, corresponding clip and clip engaging portion(s) (e.g., a snap connection), spin welding or otherwise melting together. Where the ports are removeably connected to each other, an operator may gain entry to the interior of the connector 2, 2*a* and may be able to replace components therein and/or clean the inside of the connector 2, 2*a*.

Furthermore, the first port 22 may intersect the second port 60, 60*a* and/or third port 62, 62*a* (e.g., FIG. 9) at an angle 63, 63*a* of between about 15 degrees and about 165 degrees, more preferably between about 30 degrees and about 60 degrees and, most preferably, between about 40 degrees and about 50 degrees. The second port 60, 60*a* may intersect the third port 62, 62*a* at an angle 63' between about 15 degrees and about 180 degrees, more preferably between about 90 degrees and about 180 degrees and, most preferably, 180 degrees. The angle chosen may be a consideration of various factors, including ease of injection/withdrawal of fluid, weight of the connector 2, 2*a* in a natural hanging position, and prevention of tube kinking. Moreover, the third port 62, 62*a* may intersect the side 61, 61*a* of the second port 60, 60*a* at any angle describe above.

As shown in FIGS. 1 and 2, a second port 60, 60*a* may comprise the base portion 10, 10*a* and second cap 16, 16*a*. A fluid transfer device (not shown) (e.g., an intravenous tube, syringe, catheter, or other connector) may engage the second port 60, 60*a*. For example, the second cap 16, 16*a* may have an external threaded portion 23, 23*a* (or an internal threaded portion (not shown)) to engage a corresponding threaded portion of a fluid transfer device. All means for attaching a fluid transfer device to the second port 60, 60*a*, however, are envisioned (e.g., clip and a corresponding clip engaging portion(s), tape, etc.). Such a design may allow for the fluid transfer device to be held securely onto the second port 60, 60*a* when fluid is transferred between a fluid transfer device and the second port 60, 60*a*.

Further, the base portion 10, 10*a* and second cap 16, 16*a* may define a channel 64, 64*a*. The channel 64, 64*a* may, in turn, comprise a proximal channel 66, 66*a* located at a proximal end 68, 68*a* and a main channel 70, 70*a*. The inner surface of the channel 64, 64*a* may be smooth or may have, for example, grooves, slots, protrusions, ridges or ribs. For example, one or more fluid passageways 69, 69*a* may be provided in the second cap 16, 16*a*. The fluid passageways 69, 69*a* may be one or more individual longitudinal channels or, as shown in FIGS. 1 and 2, a widened diameter portion around the entire inner surface of proximal channel 66, 66*a*. Moreover, as illustrated in FIG. 2, the main channel 70*a* may have ribs 71*a*, which may have fluid paths therebetween. Such internal structure(s) may be provided, for example, to guide the flow of fluid past the second valve element 8, 8*a*.

Furthermore, the second valve element 8, 8*a* may be positioned within second port 60, 60*a*. It should, however, be noted that one skilled in the art would appreciate that the second valve element 8, 8*a* may be any needless access device such as, for example, those disclosed in U.S. Pat. Nos. 5,676,346; 5,360,413; 5,300,034; 5,242,432; and 5,230,706. In the embodiments shown in FIGS. 1 and 2, the second valve element 8, 8*a* may comprise a head portion 72, 72*a* and a body portion 74, 74*a*. The head portion 72, 72*a* and the body portion 74, 74*a* may be one integral piece or separate pieces. And, as shown in FIGS. 1 and 2, the head portion 72, 72*a* and/or body portion 74 may be made of a solid piece of material and the body portion 74*a* may be hollow. However, the head portion 72, 72*a* or the body portion 74 may also be hollow and the body portion 74*a* may also be a solid piece of material.

As shown in FIG. 2, the body portion 74*a* may have a wall 75*a* defining an internal chamber 77*a*, which may contain fluid (e.g., air). The wall 75*a* may be solid (i.e., there are no holes or openings therethrough). As will be discuss in further detail below with regard to the use of the connector 2*a*, this construction may provide significant advantages when the air contained inside the internal chamber 77*a* may flow in and out of the connector 2*a* through one or more channels 11*a*, which may communicate with the outside of the connector 2*a*. In another embodiment where the head portion 72, 72*a* and/or body portion 74, 74*a* may be hollow, there may be one or more openings (not shown) in the head portion 72, 72*a* and/or body portion 74, 74*a*. Fluid may be able to flow through the opening(s) and into and through the head portion 72, 72*a* and/or body portion 74, 74*a*.

Further, the head portion 72, 72*a* and body portion 74, 74*a* may be made of the same or different materials such as, for example, plastic, a foam material, a composite material (i.e., made of two or more materials), a combination material (i.e., one material contained within another material) (e.g., a gel such as a hydrogel contained within rubber) or rubber (e.g., silicon polyisoprene) and may be transparent or opaque. The material may be elastomeric (i.e., compressible, stretchable, bendable, flexible, foldable or otherwise contortable). Various factors may be considered when determining the material to be used for the head portion 72, 72a and body portion 74, 74a, including compatibility with fluids flowing through the connector 2, 2a (i.e., the material does not react with fluids flowing through the connector 2, 2a) (e.g., lipid resistance), the ability to withstand sterilization/cleaning (i.e., cleaning products used in sterilization), weight, durability, resistance to bacterial formation, ease and cost of manufacturing, ability to be attached to other materials, and mechanical properties (e.g., strength, resiliency; ability to be compressed, twisted, bended, folded, or otherwise contorted). Moreover, the head portion 72, 72a and body portion 74, 74a may be formed, for example, by injection molding (e.g., liquid injection molding), casting, or extrusion and may be any shape (e.g., polygonal or spherical head; polygonal or cylindrical body).

In embodiments where the head portion 72, 72a and body portion 74, 74a may be made of separate pieces, the head portion 72, 72a and body portion 74, 74a may be connected, for example, by a bonding medium (e.g., adhesive), threads, ultrasonic welding, ultraviolet curing, spin welding or otherwise melting together.

The second valve element 8, 8a may also comprise one or more grooves, recesses, notches (e.g., notches 76, 76a) which may be located in the head portion 72, 72a and/or the body portion 74, 74a or both. As shown in FIG. 2, the body portion 74a may also comprise one or more undercuts 79a. Further, notches 76, 76a may be located anywhere on the outer surface of the head portion 72, 72a and/or body portion 74, 74a. And where the head portion 72, 72a and body portion 74, 74a are hollow, or have a wall, notches 76, 76a may be located anywhere on the inner surface of the head portion 72, 72a and/or body portion 74, 74a.

The notches 76, 76a and/or undercuts 79a may facilitate compression, bending, canting, folding, and/or contorting of the second valve element 8, 8a. In addition, compression, bending, canting, folding, and/or contorting may also be facilitated by the head portion 72, 72a and/or body portion 74, 74a being molded in a pre-cant position (such as shown in body portion 74 of FIG. 1). Moreover, the notches 76, 76a and/or undercuts 79a may assist in guiding fluid flow through the second port 60, 60a, for example, when the valve element 8, 8a is a compressed, bent, canted, folded, and/or contorted position.

The notches 76, 76a and undercuts 79a may be any shape (e.g., round, elliptical, square, rectangular or polygonal), size, and may cover any amount of area of the head portion 72, 72a and/or body portion 74, 74a. As shown in the embodiment of FIG. 1, notches 76 may be smile cuts along a portion of the outer area of both the head and body portions 72, 74. And, as shown in FIG. 2, notches 76a may be a smile cut in the head portion 72a.

The head portion 72, 72a may comprise a first enlarged portion 78, 78a which may seal opening portion 80, 80a. The head portion 72, 72a may also have a second enlarged portion 81, 81a which may engage a shoulder portion 83, 83a of the second cap 16, 16a. The enlarged portions 78, 78a and/or 81, 81a may prevent fluid from flowing past the second valve element 8, 8a.

Furthermore, a top 67, 67a of the second valve element 8, 8a may be substantially flush with respect to the top 73, 73a of the second cap 16, 16a. Such a construction may allow for antiseptic swabbing of the tops 67, 67a and 73, 73a. In another embodiment, not shown, the top 67, 67a of the second valve element 8, 8a may protrude out of the second cap 16, 16a or may be sunken into the second cap 16, 16a. These constructions may also allow for antiseptic swabbing. Where top 67, 67a of the second valve element 8, 8a may be sunken into cap 16, 16a, the top 67, 67a may be below the level of the top 73, 73a of the second cap 16, 16a. Additionally, the top 67, 67a of the second valve element 8, 8a may be flat or may have protrusions (not shown) extending therefrom. The protrusions may help guide fluid flow past the second valve element 8, 8a.

Moreover, in one exemplary embodiment (not shown), the second valve element 8 may comprise only a head portion 72 (i.e., no body portion 74). The head portion 72 may be fixed to the proximal portion 68 of the second port 60 and, in particular, may be fixed in the second cap 16. The head portion 72 may be fixed by, for example, a bonding medium (e.g., adhesive), ultrasonic welding, ultraviolet curing, spin welding or otherwise melting together. Alternatively, the head portion 72 may have one or more protruding portions (not shown) which may be engage within receiving portion(s) (not shown) in the second port 60. The head portion 72 may also have a resealable pre-slit orifice or opening (not shown) therethrough for receiving a fluid transfer device. In this way, fluid may be transferred between the fluid transfer device and the second port 60.

In another embodiment, where the second valve element 8 may only comprise a head portion 72, the head portion 72 may be a solid piece (i.e., no slits or opening therethrough) of rigid or flexible material and may have a biasing member (not shown), which may be located at a distal end 82 of the head portion 72 and may bias head portion 72 into proximal channel 66. The biasing portion may be stretchable, and may be, for example, an annular flange around the distal end 82 of the head portion 72 or one or more flange portions. It should be understood that an annular flange can be any shape (e.g., circular, square, rectangular, polygonal).

In one embodiment, the biasing member may be contained between the second cap 16 and the base portion 10 at location 84. The biasing member may have space between one or more flange portions or, where the biasing member is an annular flange, may have one or more opening therein. When a fluid transfer device is inserted into the second port 60, the head portion 72 may be pushed down into the second port 60. The biasing member and, consequently, the space and/or openings may stretch. In this embodiment, fluid may flow past the head portion 72, through the space and/or openings in the biasing member, and into main channel 70. Further, a head portion 72 made of a rigid material or containing a pin or rod therethrough (e.g., a solid piece of plastic or metal through the head portion 72) may improve the performance of this embodiment-having a rigid head portion may make it easier to stretch the biasing member upon insertion of a fluid transfer device into the second port 60.

In yet another embodiment, the second valve element 8 may be biased by a spring (not shown) positioned around the body portion 74 of the second valve element 8 and held, for example, between the enlarged portion 81 and the housing 4—including the wall of the housing 4 and any portion connected/connectable to the housing 4 (e.g., the valve support 86 (discussed below)). Alternatively, a spring may be positioned below the second valve element 8 (i.e., between the body portion 74 and the housing 4).

Referring again to FIGS. 1 and 2, the body portion 74, 74a may bias the head portion 72, 72a into the proximal channel 66, 66a. It should be understood by those skilled in the art that the body portion 74, 74a may be any structure (e.g., a spring (not shown)) which can bias the head portion 72, 72a into the proximal channel 66, 66a. Moreover, the body portion 74, 74a may be fixed or rest freely with respect to the housing 4, 4a.

For example, as shown in FIG. 2, the second valve element 8a may have a circular flange 80a. The circular flange 80a may be captured between the base portion 10a and the second cap 16a. In particular, the circular flange 80a may be captured between the base portion 10a and one or more ribs 71a of the second cap 16a. In an alternative embodiment, the second valve element 8a may have one or more flange portions. In yet another embodiment of FIG. 2, the valve element 8a may be connected to the base portion 10a, for example, by a bonding medium (e.g., adhesive), threads, ultrasonic welding, ultraviolet curing, spin welding or otherwise melting together. Such constructions may fix the second valve element 8a within the housing 4a.

Figure 10:
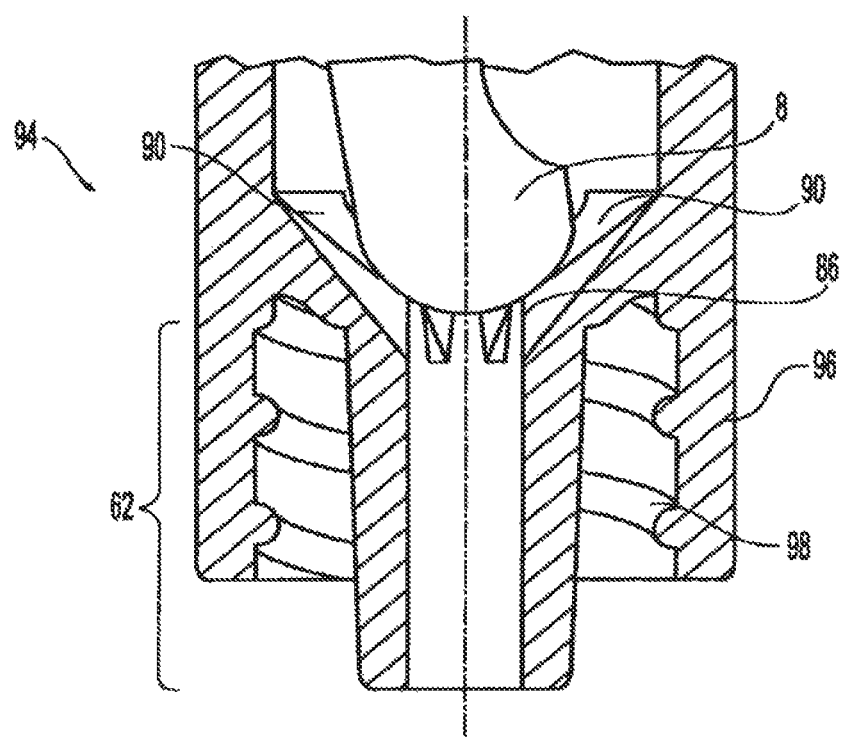
FIG. 10 is a partial cross-sectional view of an alternative exemplary embodiment of the distal portion of the connector of FIG. 1.

Alternatively, the body portion 74 may freely rest or be fixed with respect to a valve support 86. As shown in FIG. 1, the valve support 86 may be positioned in the channel 64 of the second port 60 and/or channel 88 of the third port 62. The valve support 86 may support the second valve element 8 and may comprise one or more holding ribs 90 and a valve seat 92. However, as shown in FIG. 10, in an alternative embodiment, the valve support 86 may comprise holding ribs 90 and no valve seat 92. The holding ribs 90 and/or the valve seat 92 may have a concave shape, but, any other shape may also be used. One or more fluid flow channels 93 may be located between holding ribs 90. The fluid flow channels 93 may enable fluid to flow past the second valve element 8. It should be noted, however, that the valve support 86 can be any structure located anywhere within the second and/or third ports 60, 62, so long as the valve support 86 supports the second valve element 8 and allows fluid to flow past the second valve element 8.

Further, the holding ribs 90 and the valve seat 92 may be made of metal, plastic (e.g., polycarbonate, acrylonitrile butadiene styrene (ABS)), a composite material (i.e., two or more materials) (e.g., copolyester), or rubber and may be transparent or opaque. The holding ribs 90 and the valve seat 92 may be made of the same or different materials from each other and/or the ports 60, 62. Various factors may be considered when determining the material to be used for the holding ribs 90 and the valve seat 92 including, compatibility with fluids flowing through the connector 2 (i.e., material does not chemically and/or physically react with fluids flowing through the connector 2) (e.g., lipid resistance), the ability to withstand sterilization/cleaning (i.e., cleaning products used in sterilization), weight, durability, mechanical strength, resistance to bacterial formation, ease and cost of manufacturing, and ability to be attached to other materials.

Additionally, the holding ribs 90 and/or the valve seat 92 may be integral with the surface of the channels 64, 88 or may be separate from each other and/or the channels 64, 88. If made of separate pieces, the holding ribs 90 and valve seat 92 may be connected to one another and/or channels 64, 88 by, for example, a bonding medium, threads, ultrasonic welding, ultraviolet curing, spin welding or otherwise melting together. And, if the housing 4 is designed to allow access therein, the holding ribs 90 and/or valve seat 92 may be replaceable. Moreover, in an embodiment where the third port 62 may be connected to the side 61 of the second port 60, the second valve element 8 may be supported on the wall of the housing 4 (as shown in FIG. 11) and valve support 86 may be unnecessary.

Turning now to the third port 62, 62a, the third port 62, 62a may be an integral part of the second port 60, 60a or may be attachable to the second port 60, 60a. The third port 62, 62a may be any shape (e.g., cylindrical, rectangular, polygonal) and/or size. Various factors may be considered when determining the shape of the third port 62, 62a, including compatibility with a standard fluid transfer device, the desired path of fluid flow, and the ability of the connector 2, 2a to be flushed.

FIG. 10 shows an alternative configuration of the third port 62 in the distal portion 94 of the connector 2 of FIG. 1. In this embodiment, as well as in FIG. 2, the third port 62, 62a may be surrounded by a wall portion 96, 96a which may contain internal threads 98, 98a for engaging corresponding threads (not shown) of a fluid transfer device.

Figure 11:
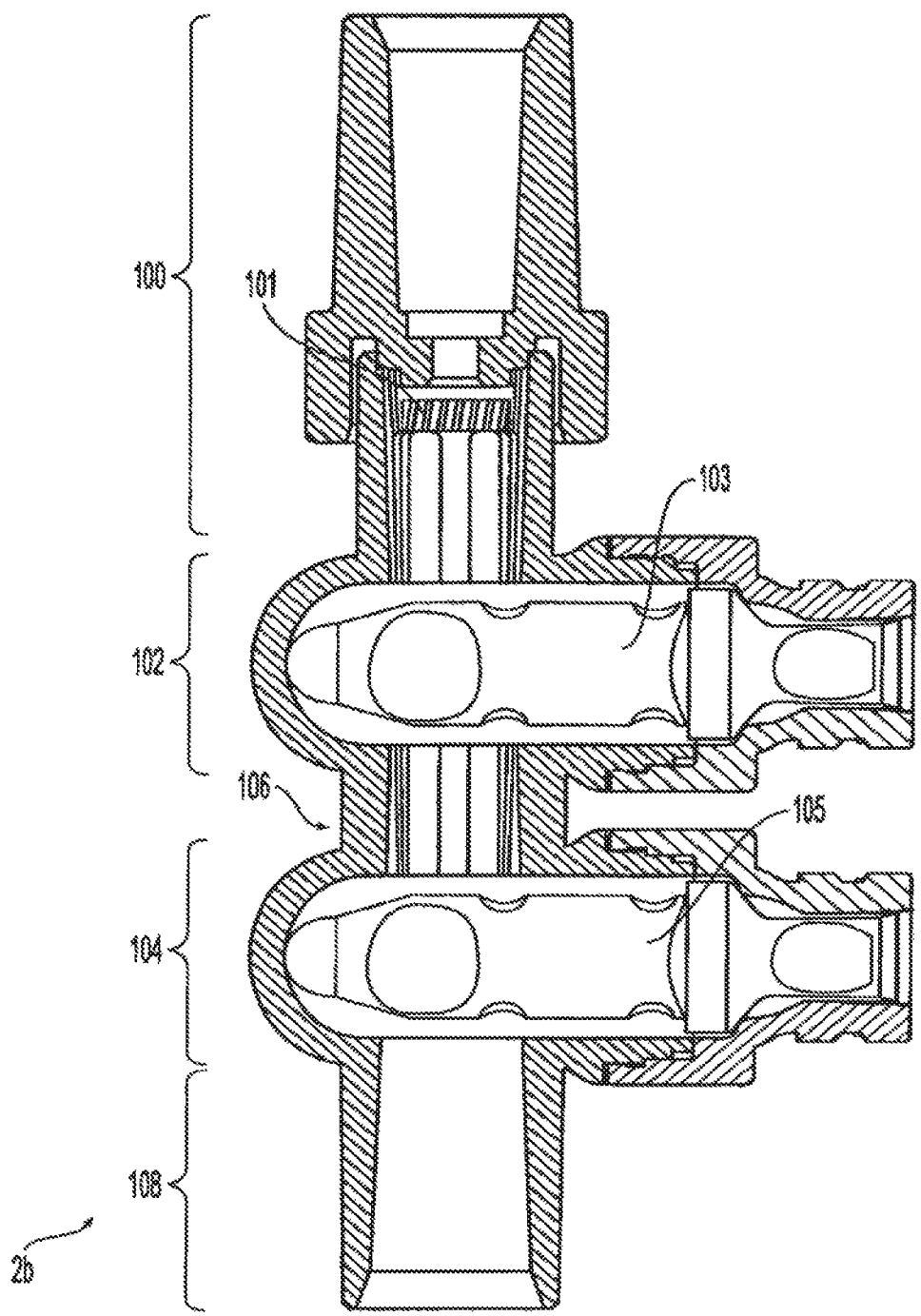
FIG. 11 is a partial cross-sectional view of an alternative exemplary embodiment of the connector of the present invention.
Figure 12:
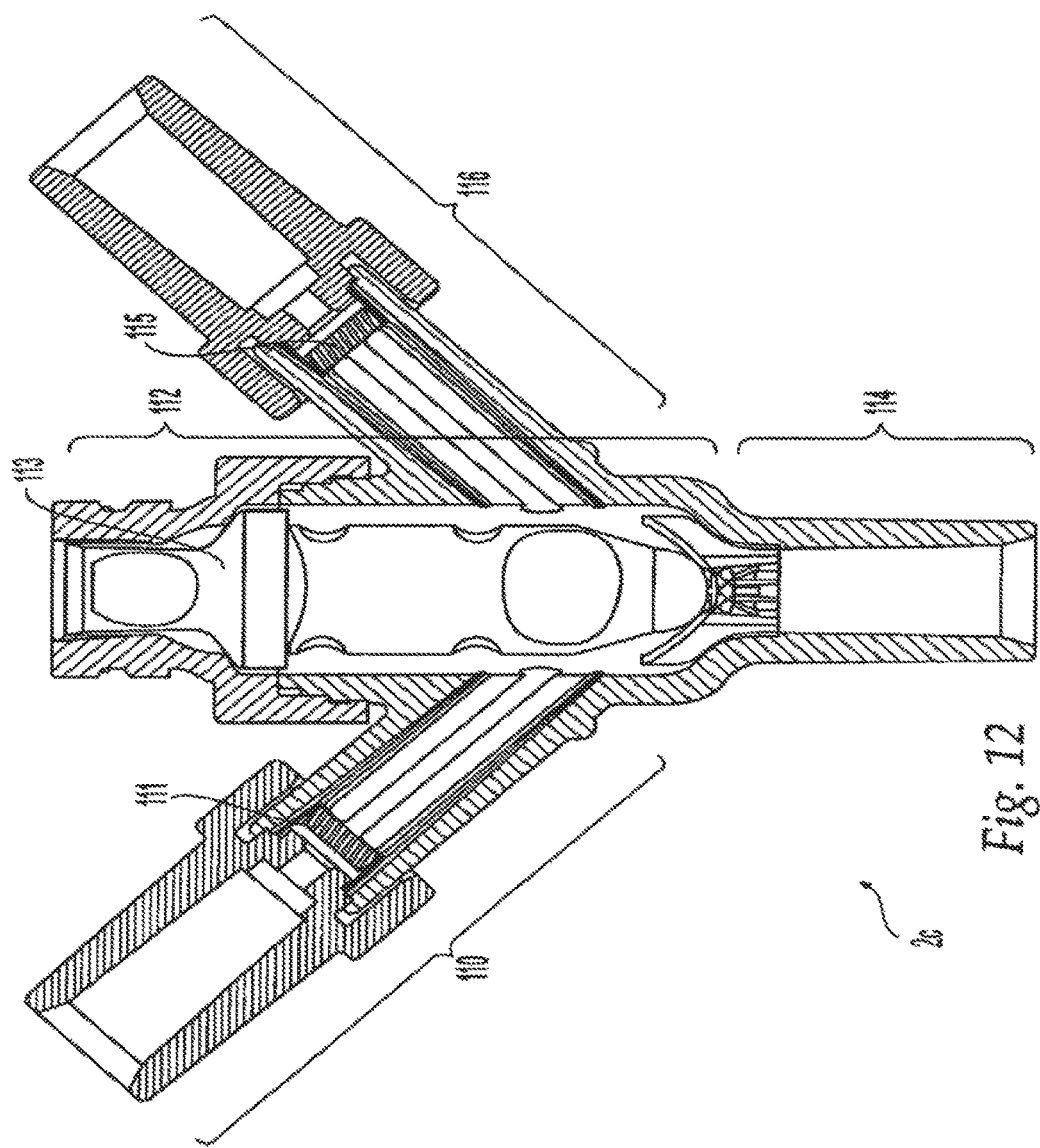
FIG. 12 is a partial cross-sectional view of an alternative exemplary embodiment of the connector of FIG. 1 with an additional port.

Furthermore, as shown in FIGS. 11 and 12, other arrangements of the first, second and third ports are also envisioned as part of the present invention. For example, the connector 2b of FIG. 11 may comprise a first port 100 having a first valve element 101, a second port 102 having a second valve element 103, a fourth port 104 having a third valve element 105, a third port or connecting port 106 between the second port 102 and fourth port 104, and a fifth port 108. The connector 2c of FIG. 12 may comprise first port 110 having a first valve element 111, a second port 112 having a second valve element 113, a third port 114, and a fourth port 116 having a third valve element 115. While the embodiments in FIGS. 11 and 12 may have more ports and valve elements than in FIGS. 1 and 2 and may have different port orientations, the ports and valve elements of FIGS. 11 and 12 may be arranged in the same orientation and configured with the same components and materials as described above with regards to the first port 22, the second port 60, 60a, the third port 62, 62a, first valve element 6 and the second valve element 8, 8a. Moreover, the connectors 2b (FIG. 11) and 2c (FIG. 12) (as well as their ports and valve elements) may function and may be used in the same way as described in detail below for FIGS. 1 and 2.

Moreover, it should be noted that any of the components of the present invention, including the specific embodiments described herein, may incorporate an antimicrobial compound or may have an antimicrobial coating covering a portion or the entire surface of the components. The antimicrobial compound or coating may inhibit the growth of bacteria. An antimicrobial material may be formed, for example, by adding a commercially available antimicrobial compound such as Agion™ produced by Agion™ Technologies Inc. of Wakefield, Mass., to, for example, plastic or rubber. This material, in turn, may be used to make a component of the present invention. Alternatively or in addition, an antimicrobial compound may be sprayed, painted or otherwise affixed to the surface of any component of the present invention and, thus, form a coating thereon.

In use, a portion of a first fluid transfer device 200, 200a (e.g., intravenous tube, syringe, catheter, or other connector) may be connected (either permanently or removeably) to the first port 22. The other end of the first fluid transfer device 200, 200a may be connected to, for example, an intravenous bag. For example, one end of an intravenous tube may be inserted into the first port 22 and the other end may be inserted into an intravenous bag. A second fluid transfer device 202, 202a, for example, another intravenous tube may connect the third port 62, 62a to a patient. The path of fluid flow from the first fluid transfer device 200, 200a, through the first port 22, the second port 60, 60a, the third port 62, 62a, and into the second fluid transfer device 202, 202a may form part of a main fluid line. As shown for example in FIGS. 1, 2, 3B, 4B, 5A and 6B, the first valve element 6 may be in a first position as a first fluid flows past the first valve element 6. The first fluid may flow through connecting channel 28, into the second port 60, 60a and through the channel 88, 88a of third port 62, 62a. In an alternative embodiment such as FIG. 9, the first fluid may flow directly from the first port 22 (e.g., through the connecting channel 28) to the third port 62, 62a. In another embodiment of the connector 2 (FIG. 1), as the first fluid flows between the second port 60 and the third port 62, the first fluid may flow through the valve support 86. In addition, in embodiments comprising the fluid channels 58, the first fluid may flow through the fluid channels 58.

Furthermore, an operator may use the second port 60, 60a to transfer a second fluid into the connector 2, 2a (e.g., into the main intravenous line) and/or transfer fluid from the connector 2, 2a. To accomplish this, a third fluid transfer device 204, 204a may be connected to the second port 60, 60a. A portion (e.g., a male luer) of the third fluid transfer device 204, 204a may be inserted into the second port 60, 60a. In the embodiments of FIGS. 1 and 2, insertion of the third fluid transfer device 204, 204a into the second port 60, 60a may result in compression, canting, bending, folding, and/or contorting of the second valve element 8, 8a within the second port 60, 60a (i.e., the head portion 72, 72a and/or body portion 74, 74a may compress, cant, bend, fold, and/or contort). In other words, the axis (not shown) of the second valve element 8, 8a may be displaced from the axis (not shown) of the second port 60, 60a. And, the top 67, 67a of the second valve element 8, 8a may move from a first position (shown in FIGS. 1 and 2), where the top 67, 67a may be substantially flush with the top 73, 73a, to a second position. It should be understood that a second position may be any position which is not the first position.

In an exemplary embodiment where the third fluid transfer device 204, 204a has threads (not shown) to engage the external threaded portion 23, 23a of the second port 60, 60a, as the third fluid transfer device 204, 204a is threaded onto the second port 60, 60a, the second valve element 8, 8a may continue to compress, cant, bend, fold, and/or contort (and possibly twist) and may move further down into the second port 60, 60a. And, as the third fluid transfer device 204, 204a moves farther into the second port 60, 60a, the second valve element 8, 8a may move out of proximal channel 66, 66a into a second position (e.g., within the main channel 70, 70a). In FIG. 2, insertion of the third fluid transfer device 204a may also result in the air contained in chamber 77a moving through channels 11a and out of connector 2a.

In a second position, fluid may flow past the second valve element 8, 8a. In an embodiment comprising the first enlarged portion 78, 78a and fluid passageways 69, 69a, fluid may flow past the second valve element 8, 8a as the first enlarged portion 78, 78a moves past the fluid passageways 69, 69a. In an embodiment where there are no fluid passageways 69, 69a, fluid may flow past the second valve element 8, 8a as the first enlarged portion 78, 78a moves out of the proximal channel 66, 66a and into the main channel 70, 70a. In an embodiment without the first enlarged portion 78, 78a fluid may flow past the second valve element 8, 8a at any time after the third fluid transfer device 204, 204a is positioned adjacent to the top 67, 67a of the second valve element 8, 8a.

Moreover, the flow of fluid between the proximal channel 66, 66a and the main channel 70, 70a may be prevented when the second enlarged portion 81, 81a engages an inner portion of the second port 60, 60a (e.g., shoulder portion 83, 83a). Upon disengagement of the second enlarged portion 81, 81a from an inner portion of the second port 60, 60a (e.g., shoulder portion 83, 83a), fluid may flow between the proximal channel 66, 66a and the main channel 70, 70a.

When the second valve element 8, 8a is in a second position, the second fluid may be transferred to the second port 60, 60a from the third fluid transfer device 204, 204a and may combine with the first fluid. It should be understood that the term "combine" can mean that the first and the second fluid join to form a homogenous third fluid (e.g., dilution of a medication in saline) or that the first and second fluids may remain separate from one another (e.g., blood in water; oil in water). Alternatively, the first fluid may be transferred to the third fluid transfer device 204, 204a from the second port 60, 60a (i.e., fluid may be withdrawn from the connector 2, 2a).

As the second fluid is transferred to the second port 60, 60a from the third transfer device 204, 204a, the first valve element 6 may move from the first position to a second position as shown, for example, in FIGS. 3A, 4A, 5B, and 6A. It should be understood that a second position may be any position that is not the first position. In a second position, fluid may be prevented from flowing past the first valve element 6 in a direction towards the first fluid transfer device 200, 200a. The movement of the first valve element 6 from the first to a second position may be the result of fluid pressure created by the transfer of the second fluid from the third fluid transfer device 204, 204a to the second port 60, 60a. Alternatively, the movement of the first valve element 6 may also result from the insertion of the third fluid transfer device 204, 204a into the second port 60, 60a.

In general, with reference to FIGS. 1 and 2, when the second fluid is transferred from the third fluid transfer device 204, 204a to the second port 60, 60a, the second fluid (along with the first fluid) may flow past the valve element 8, 8a into and through the channel 88, 88a of the third port 62, 62a and into the second fluid transfer device 202, 202a. In one embodiment of FIG. 1, fluid may pass through the channels 93 as the fluid flows between the second port 60 and the third port 62. Moreover, in the embodiment of FIG. 2, fluid may flow past the valve element 8a and flow in between ribs 71a, around the circular flange 80a via path 91a, through fluid port 93a and out channel 88a. Alternatively, fluid may flow in the opposite direction when fluid is transferred from the second port 60, 60a to the third fluid transfer device 204, 204a.

If and when the third fluid transfer device 204, 204a is removed from the second port 60, 60a, the second valve element 8, 8a may return to its first position (e.g., with the top 67, 67a of the second valve element substantially flush with the top 73, 73a). In the embodiment of FIG. 1, this may result in negative pressure (i.e., fluid within the connector 2, the first fluid transfer device 200, and/or the second fluid transfer device 202 may flow in a direction towards the opening portion 80).

In the embodiment of FIG. 2, as the second valve element 8a moves to its first position, air may flow from outside the connector 2a through channels 11a and into chamber 77a. Such a construction may result in positive pressure or self-flushing (i.e., fluid within the connector 2a, the first fluid transfer device 200a, and/or the second fluid transfer device 202a may flow in a direction 206a). It should be understood that any self-flushing construction may be integrated into the connector 2, 2a, such as those constructions disclosed in U.S. Pat. No. 5,730,41S, which is incorporated herein by reference. In both FIGS. 1 and 2, negative pressure may also occur if and when the first fluid transfer device 200, 200a is removed from the first port 22.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A connector for transferring fluid, the connector comprising:
    a base having a first port, a cap having a second port, an internal chamber defined between the base and the cap, and ribs extending longitudinally along an inner surface of the cap and between the second port and the base, the internal chamber fluidly coupled to the first and second ports; and
    a valve element having a first position and a second position within the internal chamber, the valve element comprising a head portion and a body portion, the head portion configured to seal the second port when the valve element is in the first position, the body portion having a cavity with a flange configured to be retained between the base and the cap to seal the cavity and separate the internal chamber into an air chamber in fluid communication with an outside of the connector via a passage of the base, and a liquid chamber continuously coupled to the first port regardless of the position of the valve element, wherein a fluid path extends between the ribs and the body portion of the valve element.

2. The connector of claim 1, wherein the flange is retained between an outer surface of the base and the ribs.

3. The connector of claim 1, wherein the head portion, when the valve element is in the first position, comprises a first portion in sealing contact with an inner surface of the internal chamber at a first location proximate to the second port to create a primary seal, and a second portion configured to engage a shoulder of the cap at a second location separated from the first location to create a secondary seal.

4. The connector of claim 3, wherein the second portion in sealing contact with a shoulder of the cap when the valve element is in the first position.

5. The connector of claim 1, wherein a top of the head portion is substantially flush with the second port.

6. The connector of claim 1, wherein the cap comprises a third port fluidly coupled to the internal chamber, such that the liquid chamber is continuously coupled to the third port regardless of the position of the valve element.

7. The connector of claim 1, wherein the head portion comprises a notch, such that the head portion will fold when compressed.

8. The connector of claim 7, wherein the notch comprises a portion of an elliptical shape when the valve element is viewed in cross-section.

9. The connector of claim 1, wherein the body portion comprises an inner surface having one or more notches, such that the body portion will fold when compressed.

10. The connector of claim 1, wherein the second port is configured to accept an actuator such that the valve element is compressed toward the first port in the second position.

11. The connector of claim 6, wherein the third port comprises a second valve element.

12. A connector for transferring fluid, the connector comprising:
    a housing having a first port, a second port, an internal chamber fluidly coupled to the first and second ports, and ribs extending longitudinally along an inner surface of the housing and between the first port and the second port; and
    a valve element having a first position and a second position within the internal chamber, the valve element comprising a head portion having a notch, a body portion having a cavity with an inner surface and one or more notches on the inner surface, the head portion configured to seal the second port when the valve element is in the first position, the body portion configured to seal a perimeter of the cavity to separate the internal chamber into an air chamber in fluid communication with an outside of the housing via a passage of the housing, and a liquid chamber continuously coupled to the first port regardless of the position of the valve element, wherein a fluid path extends between the ribs and the body portion of the valve element.

13. The connector of claim 12, wherein the housing comprises a third port fluidly coupled to the internal chamber, such that the liquid chamber is continuously coupled to the third port regardless of the position of the valve element.

14. The connector of claim 13, wherein the third port is coupled to the internal chamber between the first port and the valve element.

15. The connector of claim 12, wherein the second port is configured to accept an actuator such that the valve element is compressed toward the first port in the second position.

16. The connector of claim 12, wherein the body portion comprises a flange configured to be retained between a base portion and a cap portion of the housing.

17. The connector of claim 12, wherein the head portion, when the valve element is in the first position, comprises a first portion in sealing contact with an inner surface of the internal chamber at a first location proximate to the second port to create a primary seal, and a second portion configured to engage a shoulder of the housing at a second location separated from the first location to create a secondary seal.

18. The connector of claim 17, wherein the second portion in sealing contact with a shoulder of the housing when the valve element is in the first position.

19. The connector of claim 12, wherein a top of the head portion is substantially flush with the second port.

20. The connector of claim 12, wherein the notch comprises a portion of an elliptical shape when the valve element is viewed in cross-section such that the valve element will fold when compressed.

* * * * *